(12) United States Patent
Weis et al.

(10) Patent No.: US 9,206,454 B2
(45) Date of Patent: Dec. 8, 2015

(54) PROTEIN EXPRESSION

(75) Inventors: Roland Weis, Grambach (AT); Thomas Purkarthofer, Grambach (AT)

(73) Assignee: VTU HOLDING GMBH, Grambach (AT)

( * ) Notice: Subject to any disclaimer, the term of this patent is extended or adjusted under 35 U.S.C. 154(b) by 0 days.

(21) Appl. No.: 14/241,505

(22) PCT Filed: Aug. 31, 2012

(86) PCT No.: PCT/EP2012/066949
§ 371 (c)(1),
(2), (4) Date: Feb. 27, 2014

(87) PCT Pub. No.: WO2013/030329
PCT Pub. Date: Mar. 7, 2013

(65) Prior Publication Data
US 2014/0212923 A1    Jul. 31, 2014

(30) Foreign Application Priority Data
Aug. 31, 2011   (EP) .................................... 11179496

(51) Int. Cl.
| | |
|---|---|
| C12P 21/02 | (2006.01) |
| C12P 21/00 | (2006.01) |
| C07K 14/55 | (2006.01) |
| C07K 14/765 | (2006.01) |
| C07K 14/79 | (2006.01) |
| C12N 9/04 | (2006.01) |
| C12N 9/90 | (2006.01) |
| C12N 15/81 | (2006.01) |

(52) U.S. Cl.
CPC ................. *C12P 21/00* (2013.01); *C07K 14/55* (2013.01); *C07K 14/765* (2013.01); *C07K 14/79* (2013.01); *C12N 9/0006* (2013.01); *C12N 9/90* (2013.01); *C12N 15/815* (2013.01); *C12P 21/02* (2013.01); *C12Y 101/03013* (2013.01); *C12Y 503/04001* (2013.01)

(58) Field of Classification Search
None
See application file for complete search history.

(56) References Cited

U.S. PATENT DOCUMENTS 5,773,245 A * 6/1998 Wittrup et al. ................ 435/69.1

FOREIGN PATENT DOCUMENTS

| WO | 93/25676 A1 | 12/1993 |
|---|---|---|
| WO | 94/08012 A1 | 4/1994 |
| WO | 2006/089329 A1 | 8/2006 |
| WO | 2009/105357 A1 | 8/2009 |

OTHER PUBLICATIONS

Robinson AS, et al., Protein Disulfide Isomerase Overexpression Increases Secretion of Foreign Proteins in Saccharomyces Cerevisiae, Nature Biotechnology, 12:381-384 (1994).
Schultz LD, et al., Using molecular genetics to improve the production of recombinant proteins by the yeast Saccharomyces cerevisiae, New York Academy of Sciences, 721:148-157 (1994).
Smith Jason D et al., Protein disulfide isomerase, but not binding protein, overexpression enhances secretion of a non-disulfide-bonded protein in yeast, Biotechnology and Bioengineering, 85:340-350 (2004).
Subramanian Shoba et al., Pbn1p: An essential endoplasmic reticulum membrane protein required for protein processing in the endoplasmic reticulum of budding yeast, Proceedings of the National Academy of Sciences of the United States of America, 103:939-944 (2006).
Longtine Mark S et al., Additional modules for versatile and economical PCR-based gene deletion and modification in Saccharomyces cerevisiae, Yeast, 14:953-961(1998).
Schroder, Martin, Engineering eukaryotic protein factories, Biotechnology Letters, 30:187-196 (2007).
International Preliminary Report on Patentability for International Appl. No. PCT/EP2012/066949 (with annexes), European Patent Office, Aug. 21, 2013.

* cited by examiner

*Primary Examiner* — Jim Ketter
(74) *Attorney, Agent, or Firm* — Nevrivy Patent Law Group P.L.L.C.

(57) ABSTRACT

The present invention relates to a genetically modified yeast cell comprising: —at least one recombinant promoter operably linked to at least one gene encoding a polypeptide or protein supporting the biosynthesis of polypeptides or proteins within said cell, said at least one gene being located at the native genomic locus of the genetically unmodified wild-type yeast cell, wherein the naturally occurring promoter of the at least one gene encoding the biosynthesis supporting polypeptide or protein is inactivated by at least one mutation within said naturally occurring promoter and, —a secretion cassette comprising a recombinant nucleic acid molecule encoding a protein or polypeptide of interest and a method for producing a recombinant protein or polypeptide of interest using such a cell.

28 Claims, 7 Drawing Sheets

SEQUENCE LISTING

<160> NUMBER OF SEQ ID NOS: 21

<210> SEQ ID NO 1
<211> LENGTH: 953
<212> TYPE: DNA
<213> ORGANISM: Artificial Sequence
<220> FEATURE:
<223> OTHER INFORMATION: Nucleic acid sequence comprising the wild type AOX1 promoter of Pichia pastoris

<400> SEQUENCE: 1

```
ggtaccagat ctaacatcca aagacgaaag gttgaatgaa accttttgc catccgacat      60
ccacaggtcc attctcacac ataagtgcca aacgcaacag gaggggatac actagcagca    120
gaccgttgca aacgcaggac ctccactcct cttctcctca acacccactt ttgccatcga    180
aaaaccagcc cagttattgg gcttgattgg agctcgctca ttccaattcc ttctattagg    240
ctactaacac catgacttta ttagcctgtc tatcctggcc ccctggcga ggttcatgtt     300
tgtttatttc cgaatgcaac aagctccgca ttacacccga acatcactcc agatgagggc    360
tttctgagtg tggggtcaaa tagtttcatg ttccccaaat ggcccaaaac tgacagttta    420
aacgctgtct tggaacctaa tatgacaaaa gcgtgatctc atccaagatg aactaagttt    480
ggttcgttga aatgctaacg gccagttggt caaaagaaa cttccaaaag tcggcatacc    540
gtttgtcttg tttggtattg attgacgaat gctcaaaaat aatctcatta atgcttagcg    600
cagtctctct atcgcttctg aaccccggtg cacctgtgcc gaaacgcaaa tggggaaaca    660
cccgcttttt ggatgattat gcattgtctc cacattgtat gcttccaaga ttctggtggg    720
aatactgctg atagcctaac gttcatgatc aaaatttaac tgttctaacc cctacttgac    780
agcaatatat aaacagaagg aagctgccct gtcttaaacc tttttttta tcatcattat    840
tagcttactt tcataattgc gactggttcc aattgacaag cttttgattt taacgacttt    900
taacgacaac ttgagaagat caaaaaacaa ctaattattg aaagaattca acc           953
```

<210> SEQ ID NO 2
<211> LENGTH: 2840
<212> TYPE: DNA
<213> ORGANISM: Artificial Sequence
<220> FEATURE:

<223> OTHER INFORMATION: Artificial Sequence comprising nucleic acid
sequences derived from Pichia pastoris

<400> SEQUENCE: 2

```
aagggagaca tattcggcta ttgtttactt tgcgcccaca gtagcgttaa gaaacattgt      60
ttgttcgatt tattgggctg ttgataaatt caattgatta cgttcgcata ctagctatca     120
taaactaagc accaccttac accactttct cactgaagat tttcgacatc aaatttctct     180
tggatcacca tcaaccttgt gtctacatgt ccttgtcttt gaacctaaat cagatagccg     240
tgcgggttgt gggcatattg cctcgtattc cggagattca cattgccatt cctaatattt     300
ttcagcgacg caccgaagct tctacagaga ctcacgatcc tcgcatacta gagctgatag     360
aaaatctaca ggatgccgag gttcctccat tcttcattga taacggtata cttaaagcag     420
caccaaaaaa gaaggtttct catatgaaaa gacgccagaa attatatggt ccaggaaaaa     480
aacaactctc tttactacaa aatttgaaca ggtgtcctgc ctgcggaaac tacaaacgat     540
cacacaccct ctgcatgcat tgcgtaggac aaatcaggag acattggaac gactctgttc     600
ctcaacagga ggcatttcgt gaagagtttg ttaatccttt ggatgagaag attctttatc     660
caggaaagaa agaactgccc gatgaacgaa ctttacgtaa aaggagtgg ctgaagagaa     720
gaccccgaac actccctgtt gaatagaaca cgaacactgt aaatagaata aagaaaact     780
tggatagtag aacttcaatg tagtgttct attgtcttac gcggctcttt agattgcaat     840
ccccagaatg gaatcgtcca tctttctcaa cccactcaaa gataatctac cagacatacc     900
tacgccctcc atcccagcac cacgtcgcga tcacccctaa aacttcaata attgaacacg     960
tactgatttc caaaccttct tcttcttcct atctataaga agatctaaca tccaaagacg    1020
aaaggttgaa tgaaaccttt ttgccatccg acatccacag gtccattctc acacataagt    1080
gccaaacgca acaggaggg atacactagc agcagaccgt tgcaaacgca ggacctccac    1140
tcctcttctc ctcaacaccc acttttgcca tcgaaaaacc agcccagtta ttgggcttga    1200
ttggagctcg ctcattccaa ttccttctat taggctacta acaccatgac tttattagcc    1260
tgtctatcct ggcccccctg gcgaggttca tgtttgttta tttccgaatg caacaagctc    1320
cgcattacac ccgaacatca ctccagatga gggcttctg agtgtggggt caaatagttt    1380
catgttcccc aaatggccca aaactgacag tttaaacgct gtcttggaac ctaatatgac    1440
aaaagcgtga tctcatccaa gatgaactaa gtttggttcg ttgaaatgct aacggccagt    1500
tggtcaaaaa gaaacttcca aaagtcggca taccgtttgt cttgtttggt attgattgac    1560
gaatgctcaa aaataatctc attaatgctt agcgcagtct ctctatcgct tctgaacccc    1620
ggtgcacctg tgccgaaacg caaatgggga acacccgct ttttggatga ttatgcattg    1680
tctccacact gctgatagcc taacgttcat gatcaaaatt taactgttct aacccctact    1740
tgacagcaat atataaacag aaggaagctg ccctgtctta aaccttttt tttatcatca    1800
ttattagctt actttcataa ttgcgactgg ttccaattga caagctttg attttaacga    1860
cttttaacga caacttgaga agatcaaaaa acaactaatt attgaaagaa gttcctatac    1920
tttctagaga ataggaactt ccgaaacgat gcaattcaac tggaatatta aaactgtggc    1980
aagtattttg tccgctctca cactagcaca agcaagtgat caggaggcta ttgctccaga    2040
ggactctcat gtcgtcaaat tgactgaagc cacttttgag tctttcatca ccagtaatcc    2100
tcacgttttg gcagagtttt ttgccccttg gtgtggtcac tgtaagaagt tgggccctga    2160
acttgtttct gctgccgaga tcttaaagga caatgagcag gttaagattg ctcaaattga    2220
```

-continued

```
ttgtacggag gagaaggaat tatgtcaagg ctacgaaatt aaagggtatc ctactttgaa    2280
ggtgttccat ggtgaggttg aggtcccaag tgactatcaa ggtcaaagac agagccaaag    2340
cattgtcagc tatatgctaa agcagagttt accccctgtc agtgaaatca atgcaaccaa    2400
agatttagac gacacaatcg ccgaggcaaa agagcccgtg attgtgcaag tactaccgga    2460
agatgcatcc aacttggaat ctaacaccac attttacgga gttgccggta ctctcagaga    2520
gaaattcact tttgtctcca ctaagtctac tgattatgcc aaaaaataca ctagcgactc    2580
gactcctgcc tatttgcttg tcagacctgg cgaggaacct agtgtttact ctggtgagga    2640
gttagatgag actcatttgg tgcactggat tgatattgag tccaaacctc tatttggaga    2700
cattgacgga tccaccttca aatcatatgc tgaagctaac atccctttag cctactattt    2760
ctatgagaac gaagaacaac gtgctgctgc tgccgatatt attaaacctt ttgctaaaga    2820
gcaacgtggc aaaattaact                                                2840

<210> SEQ ID NO 3
<211> LENGTH: 2040
<212> TYPE: DNA
<213> ORGANISM: Artificial Sequence
<220> FEATURE:
<223> OTHER INFORMATION: Artificial Sequence encoding human transferrin

<400> SEQUENCE: 3
gttccagata agactgttag atggtgtgct gtttcagagc atgaggctac taaatgtcaa      60
tcttttagag atcacatgaa gtctgtcatc ccatctgatg gtccatccgt ggcttgtgtg     120
aagaaagctt cttaccttga ttgtatccgg gccatcgctg ctaacgaagc tgacgcagtc     180
accttggacg cgggtttagt gtacgacgca tatctagccc caaacaactt aaagccagtt     240
gtcgctgagt tttacggtag caaggaagat ccacagacat tctactacgc cgtcgctgtt     300
gtgaaaaagg actccggttt tcaaatgaac cagcttagag ggaagaagtc atgtcatacc     360
ggacttggaa gatcagctgg ttggaacatt ccaatcggtt tgctgtattg cgatcttcca     420
gagccacgga agcctttgga aaggctgtt gctaatttct tttctggttc atgtgctccc     480
tgtgccgacg gtaccgactt ccacagttg tgccagctgt gtccaggctg cggttgttca     540
acattaaacc aatacttcgg ttactccggt gcgttcaagt gccttaagga cggtgctggt     600
gatgttgcgt tgttaaaaca ttccactatt ttcgagaacc tggcaaataa agcagataga     660
gatcaatacg aactgttatg cctagataac actagaaaac ctgttgacga gtacaaggac     720
tgtcaccttg cccaagtgcc atctcacact gttgttgcca gatcgatggg tggtaaagag     780
gaccttattt gggagttgct gaaccaagct caagaacact tcggaaagga caagtcaaag     840
gaatttcaat tgttttcttc tcctcacgga aaggatttgc tttttaagga ttctgctcat     900
ggtttcttga aggtcccacc aagaatggat gcaaaaatgt accttggtta cgagtacgta     960
actgcgatta gaaatttaag agaaggtacg tgtccagaag ccccaactga tgaatgtaag    1020
ccagttaaat ggtgtgcatt gtctcaccac gaaagattga agtgtgacga atggtctgtg    1080
aactcagttg gtaaaattga gtgtgtgtcg gccgaaacta cggaagattg tattgcaaag    1140
atcatgaacg gagaagcaga tgccatgtca ctcgacggag gtttcgtgta tattgccggt    1200
aagtgtggcc ttgttccagt tttggcagag aactacaaca atccgataaa ctgtgaagac    1260
actcctgagg ctggctactt cgcagttgct gttgttaaaa agtctgcttc ggacctaacc    1320
tgggacaacc tgaagggtaa gaagtcttgt cacaccgcag tcgggagaac cgcaggatgg    1380
aacatcccaa tgggtcttct ttacaataag atcaaccact gtaggtttga cgagttcttt    1440
```

```
tctgaaggtt gtgctcctgg atctaagaag gactcctctc tttgtaaact gtgtatggga    1500
tctggtttga acttgtgcga gccaaacaac aaggaaggtt attacggtta caccggagct    1560
tttagatgtt tggttgaaaa gggagacgtt gccttcgtca acaccaaac tgtgcctcag     1620 aacactggtg gtaagaaccc cgatccttgg gcaaagaatt tgaacgagaa ggattacgag    1680
ttattatgtt tggacggtac ccgtaaacca gttgaagaat acgccaattg tcacttggct    1740
agagcaccaa accacgccgt cgtgactaga aaagataagg aggcttgtgt tcacaagatt    1800
ttgcgtcaac aacaacattt gtttggatct aacgttactg attgttctgg taacttctgt    1860
ttgttccgta gcgagactaa ggatctgtta tttagggacg acaccgtttg cctggccaag    1920
ttgcacgacc gtaacactta cgagaagtat ttaggagagg aatacgtgaa ggccgttggc    1980
aatttgagaa agtgctctac ctcttctctt ttagaagcct gtacctttag aagaccttaa    2040

<210> SEQ ID NO 4
<211> LENGTH: 2040
<212> TYPE: DNA
<213> ORGANISM: Artificial Sequence
<220> FEATURE:
<223> OTHER INFORMATION: Artificial Sequence encoding human transferrin

<400> SEQUENCE: 4
gttccagata agactgttag atggtgtgct gtttcagagc atgaggctac taaatgtcaa      60
tcttttagag atcacatgaa gtctgtcatc ccatctgatg gtccatccgt ggcttgtgtg     120
aagaaagctt cttaccttga ttgtatccgg gccatcgctg ctaacgaagc tgacgcagtc     180
accttggacg cgggtttagt gtacgacgca tatctagccc caaacaactt aaagccagtt     240
gtcgctgagt tttacggtag caaggaagat ccacagacat tctactacgc cgtcgctgtt     300
gtgaaaaagg actccggttt tcaaatgaac cagcttagag ggaagaagtc atgtcatacc     360
ggacttggaa gatcagctgg ttggaacatt ccaatcggtt tgctgtattg cgatcttcca     420
gagccacgga agcctttgga aaggctgtt gctaatttct tttctggttc atgtgctccc     480
tgtgccgacg gtaccgactt ccacagttg tgccagctgt gtccaggctg cggttgttca     540 acattaaaacc aatacttcgg ttactccggt gcgttcaagt gccttaagga cggtgctggt     600
gatgttgcgt tgttaaaaca ttccactatt ttcgagaacc tggcaaataa agcagataga     660
gatcaatacg aactgttatg cctagataac actagaaaac tgttgacga gtacaaggac     720 tgtcaccttg cccaagtgcc atctcacact gttgttgcca gatcgatggg tggtaaagag     780
gaccttattt gggagttgct gaaccaagct caagaacact tcggaaagga caagtcaaag     840
gaatttcaat tgttttcttc tcctcacgga aaggatttgc tttttaagga ttctgctcat     900
ggtttcttga aggtcccacc aagaatggat gcaaaaatgt accttggtta cgagtacgta     960
actgcgatta gaaattaag agaaggtacg tgtccagaag ccccaactga tgaatgtaag    1020
ccagttaaat ggtgtgcatt gtctcaccac gaaagattga gtgtgacga atggtctgtg    1080 aactcagttg gtaaaattga gtgtgtgtcg gccgaaacta cggaagattg tattgcaaag    1140
atcatgaacg gagaagcaga tgccatgtca ctcgacggag gtttcgtgta tattgccggt    1200
aagtgtggcc ttgttccagt tttggcagag aactaccaaa aatccgataa ctgtgaagac    1260
actcctgagg ctggctactt cgcagttgct gttgttaaaa agtctgcttc ggacctaacc    1320
tgggacaacc tgaagggtaa gaagtcttgt cacaccgcag tcgggagaac cgcaggatgg    1380
aacatcccaa tgggtctcc ttacaataag atcaaccact gtaggtttga cgagttctt    1440
```

```
tctgaaggtt gtgctcctgg atctaagaag gactcctctc tttgtaaact gtgtatggga    1500
tctggtttga acttgtgcga gccaaacaac aaggaaggtt attacggtta caccggagct    1560
tttagatgtt tggttgaaaa gggagacgtt gccttcgtca acaccaaac tgtgcctcag     1620 aacactggtg gtaagaaccc cgatccttgg gcaaagaatt tgaacgagaa ggattacgag    1680
ttattatgtt tggacggtac ccgtaaacca gttgaagaat acgccaattg tcacttggct    1740
agagcaccaa accacgccgt cgtgactaga aaagataagg aggcttgtgt tcacaagatt    1800
ttgcgtcaac aacaacattt gtttggatct caagttactg attgttctgg taacttctgt    1860
ttgttccgta gcgagactaa ggatctgtta tttagggacg acaccgtttg cctggccaag    1920
ttgcacgacc gtaacactta cgagaagtat ttaggagagg aatacgtgaa ggccgttggc    1980
aatttgagaa agtgctctac ctcttctctt ttagaagcct gtacctttag aagaccttaa    2040
```

<210> SEQ ID NO 5
<211> LENGTH: 2182
<212> TYPE: DNA
<213> ORGANISM: Artificial Sequence
<220> FEATURE:
<223> OTHER INFORMATION: Artificial Sequence comprising nucleic acid
      sequences derived from Pichia pastoris

<400> SEQUENCE: 5

```
aagggagaca tattcggcta ttgtttactt tgcgcccaca gtagcgttaa gaaacattgt      60
ttgttcgatt tattgggctg ttgataaatt caattgatta cgttcgcata ctagctatca     120
taaactaagc accaccttac accactttct cactgaagat tttcgacatc aaatttctct     180
tggatcacca tcaaccttgt gtctacatgt ccttgtcttt gaacctaaat cagatagccg     240
tgcgggttgt gggcatattg cctcgtattc cggagattca cattgccatt cctaatattt     300
ttcagcgacg caccgaagct tctacagaga ctcgaagttc ctatactttc tagagaatag     360
gaacttcaga tctaacatcc aaagacgaaa ggttgaatga aaccttttg ccatccgaca      420 tccacaggtc cattctcaca cataagtgcc aaacgcaaca ggaggggata cactagcagc     480
agaccgttgc aaacgcagga cctccactcc tcttctcctc aacacccact tttgccatcg     540
aaaaaccagc ccagttattg ggcttgattg gagctcgctc attccaattc cttctattag     600
gctactaaca ccatgacttt attagcctgt ctatcctggc cccctggcg aggttcatgt       660 tgtttatttt ccgaatgcaa caagctccgc attacacccg aacatcactc cagatgaggg     720 cttctctgagt gtggggtcaa atagtttcat gttccccaaa tggcccaaaa ctgacagttt    780
aaacgctgtc ttggaaccta atatgacaaa agcgtgatct catccaagat gaactaagtt     840
tggttcgttg aaatgctaac ggccagttgg tcaaaaagaa acttccaaaa gtcggcatac     900
cgtttgtctt gtttggtatt gattgacgaa tgctcaaaaa taatctcatt aatgcttagc     960
gcagtctctc tatcgcttct gaaccccggt gcacctgtgc cgaaacgcaa atggggaaac    1020
acccgctttt tggatgatta tgcattgtct ccacactgct gatagcctaa cgttcatgat    1080
caaaatttaa ctgttctaac ccctacttga cagcaatata taaacagaag gaagctgccc    1140
tgtcttaaac ctttttttt atcatcatta ttagcttact ttcataattg cgactggttc     1200
caattgacaa gcttttgatt ttaacgactt ttaacgacaa cttgagaaga tcaaaaaaca    1260
actaattatt gaattccgaa acgatgcaat tcaactggaa tattaaaact gtggcaagta    1320
ttttgtccgc tctcacacta gcacaagcaa gtgatcagga ggctattgct ccagaggact    1380
ctcatgtcgt caaattgact gaagccactt ttgagtcttt catcaccagt aatcctcacg    1440
```

| | |
|---|---|
| ttttggcaga gttttttgcc ccttggtgtg gtcactgtaa aagttgggc cctgaacttg | 1500 |
| tttctgctgc cgagatttta aaggacaatg agcaggttaa gattgctcaa attgattgta | 1560 |
| cggaggagaa ggaattatgt caaggctacg aaattaaagg gtatcctact ttgaaggtgt | 1620 |
| tccatggtga ggttgaggtc ccaagtgact atcaaggtca aagacagagc caaagcattg | 1680 |
| tcagctatat gctaaagcag agtttacccc ctgtcagtga aatcaatgca accaaagatt | 1740 |
| tagacgacac aatcgccgag gcaaaagagc ccgtgattgt gcaagtacta cctgcagcgg | 1800 |
| aagatgcatc caacttggaa tctaacacca cattttacgg agttgccggt actctcagag | 1860 |
| agaaattcac ttttgtctcc actaagtcta ctgattatgc caaaaaatac actagcgact | 1920 |
| cgactcctgc ctatttgctt gtcagacctg gcgaggaacc tagtgtttac tctggtgagg | 1980 |
| agttagatga gactcatttg gtgcactgga ttgatattga gtccaaacct ctatttggag | 2040 |
| acattgacgg atccaccttc aaatcatatg ctgaagctaa catcccttta gcctactatt | 2100 |
| tctatgagaa cgaagaacaa cgtgctgctg ctgccgatat tattaaaccct tttgctaaag | 2160 |
| agcaacgtgg caaaattaac tt | 2182 |

<210> SEQ ID NO 6
<211> LENGTH: 402
<212> TYPE: DNA
<213> ORGANISM: Artificial Sequence
<220> FEATURE:
<223> OTHER INFORMATION: Artificial Sequence encoding human
      interleukin-2

<400> SEQUENCE: 6

| | |
|---|---|
| gcaccaacct cttcttctac gaaaaagact cagcttcaat tggagcacct tttactggac | 60 |
| ttgcaaatga tcctgaacgg tatcaacaac tacaaaaacc ctaaacttac tagaatgttg | 120 |
| accttcaagt tttacatgcc aaagaaggct accgaattga agcacttgca atgtctggag | 180 |
| gaggagttga agccattgga agaagttttg aacttggcac agtcgaagaa cttccacctt | 240 |
| agacctagag acttgatttc taacatcaac gtcatcgtcc tggagcttaa ggggtccgag | 300 |
| actactttca tgtgtgagta cgctgacgag acagcgacta ttgtcgagtt cttgaataga | 360 |
| tggatcactt tcgcccaatc cattatctcc accttaacct aa | 402 |

<210> SEQ ID NO 7
<211> LENGTH: 1758
<212> TYPE: DNA
<213> ORGANISM: Artificial Sequence
<220> FEATURE:
<223> OTHER INFORMATION: Artificial Sequence encoding human serum
      albumin

<400> SEQUENCE: 7

| | |
|---|---|
| gatgcacaca atcagaagt tgctcataga ttcaaggacc tcggagaaga gaacttcaag | 60 |
| gctcttgtcc ttatcgcttt cgctcaatac cttcagcaat gtccttttga ggaccacgtt | 120 |
| aagttggtga acgaagttac cgagttcgct aaaacttgcg tagctgacga atctgctgag | 180 |
| aactgtgaca agtcacttca cactcttttt ggtgacaagc tttgtactgt cgctacccct | 240 |
| cgtgaaaacct acggcgaaat ggccgattgc tgtgctaagc aggaacctga agaaaacgaa | 300 |
| tgtttcttgc agcacaagga cgataacccc aatcttcctc gtttggttcg tcctgaggtc | 360 |
| gacgttatgt gcaccgcttt tcatgacaac gaagagactt tcttaaagaa ataccttttac | 420 |
| gaaatcgctc gtcgtcaccc atacttctac gctccagagc tgttgttctt cgcaaagaga | 480 |
| tataaggctg ctttcactga gtgttgccaa gctgctgaca aggcagcttg tctattgcct | 540 |

```
aagcttgacg aattgcgaga tgagggtaaa gcatcttccg ccaagcagag attgaaatgc    600
gcttccttgc agaagtttgg tgagcgagct ttcaaagcct gggccgtggc taggttgagc    660
caacgttttc ctaaagctga gttcgctgaa gtttctaagt tggttactga tcttactaag    720
gtgcacactg aatgttgcca cggtgacctt ctggagtgtg ctgatgaccg tgcagatttg    780
gctaagtata tttgtgaaaa ccaagattct atttcttcta aactaaagga atgttgtgaa    840
aagccacttc ttgagaaaag tcactgtatc gctgaggtgg agaacgacga gatgccagct    900
gaccttccta gcctggctgc tgatttcgtt gaatctaagg acgtatgcaa gaattacgca    960
gaggccaagg atgttttcct tggcatgttt ttgtacgagt acgctagaag acaccctgac   1020
tactccgtag ttctcttgct gaggttggca aagacctacg agactaccct agagaagtgt   1080
tgcgccgcag ctgatcctca cgagtgttat gctaaagttt ttgatgagtt taaacctttg   1140
gttgaggagc cacaaaactt gattaagcag aactgcgagc ttttcgaaca attgggggaa   1200
tacaagttcc aaaatgcctt gctagtcagg tacaccaaaa aggtccctca ggtcagcacc   1260
ccaaccttag tcgaggtgtc cagaaatttg ggcaaagttg ttctaaatg ttgcaagcac    1320 ccagaagcta agaggatgcc atgtgccgaa gactaccttt ccgtcgttct gaaccaactc   1380
tgtgttttgc acgaaaagac tccagtctca gaccgtgtca cgaaatgttg taccgagtct   1440
ctggttaaca aagaccttg tttctctgct ttggaagttg acgaaactta cgtcccaaag    1500
gagttcaacg cggagacttt caccttccac gccgacattt gtacactttc cgagaaggaa   1560
agacaaatca gaagcaaac cgcactagtt gaattggtta acataagcc taaggctacc    1620 aaagaacaat tgaaagcagt tatggatgat tttgcggctt tcgtggaaaa gtgttgtaag   1680
gctgatgaca aggaaacctg tttcgccgaa gaaggtaaga agttagtcgc cgcctctcag   1740
gctgctcttg gactgtaa                                                 1758
```

<210> SEQ ID NO 8
<211> LENGTH: 18
<212> TYPE: DNA
<213> ORGANISM: Artificial Sequence
<220> FEATURE:
<223> OTHER INFORMATION: Synthesized Artificial Sequence

<400> SEQUENCE: 8

```
cagcacacca tctaacag                                                    18
```

<210> SEQ ID NO 9
<211> LENGTH: 18
<212> TYPE: DNA
<213> ORGANISM: Artificial Sequence
<220> FEATURE:
<223> OTHER INFORMATION: Synthesized Artificial Sequence

<400> SEQUENCE: 9

```
ggtccttgaa tctatgag                                                    18
```

<210> SEQ ID NO 10
<211> LENGTH: 18
<212> TYPE: DNA
<213> ORGANISM: Artificial Sequence
<220> FEATURE:
<223> OTHER INFORMATION: Synthesized Artificial Sequence

<400> SEQUENCE: 10

```
cgtagaagaa gaggttgg                                                    18
```

<210> SEQ ID NO 11
<211> LENGTH: 89
<212> TYPE: PRT
<213> ORGANISM: Artificial Sequence
<220> FEATURE:
<223> OTHER INFORMATION: Artificial Sequence from Saccharomyces
      cerevisiae

<400> SEQUENCE: 11

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala
                 85
```

<210> SEQ ID NO 12
<211> LENGTH: 265
<212> TYPE: DNA
<213> ORGANISM: Artificial Sequence
<220> FEATURE:
<223> OTHER INFORMATION: Artificial Sequence from Saccharomyces
      cerevisiae

<400> SEQUENCE: 12

```
atgagattcc catctatttt caccgctgtc ttgttcgctg cctcctctgc attggctgcc      60
cctgttaaca ctaccactga agacgagact gctcaaattc agctgaagc agttatcggt      120 tactctacct tgagggtgat ttcgacgtcg ctgttttgcc tttctctaac tccactaaca     180
acggtttgtt gttcattaac accactatcg cttccattgc tgctaaggaa gagggtgtct     240
ctctcgagaa gaagaggccg aagct                                           265
```

<210> SEQ ID NO 13
<211> LENGTH: 19
<212> TYPE: DNA
<213> ORGANISM: Artificial Sequence
<220> FEATURE:
<223> OTHER INFORMATION: Synthesized Artificial Sequence

<400> SEQUENCE: 13

```
cttgaaccca atgagtgtg                                                   19
```

<210> SEQ ID NO 14
<211> LENGTH: 19
<212> TYPE: DNA
<213> ORGANISM: Artificial Sequence
<220> FEATURE:
<223> OTHER INFORMATION: Synthesized Artificial Sequence

<400> SEQUENCE: 14

```
gaagctgaag aagaagctg                                                   19
```

<210> SEQ ID NO 15
<211> LENGTH: 20
<212> TYPE: DNA
<213> ORGANISM: Artificial Sequence

```
<220> FEATURE:
<223> OTHER INFORMATION: Synthesized Artificial Sequence

<400> SEQUENCE: 15
gattgtcgca cctgattgcc                                                     20

<210> SEQ ID NO 16
<211> LENGTH: 2253
<212> TYPE: DNA
<213> ORGANISM: Artificial Sequence
<220> FEATURE:
<223> OTHER INFORMATION: Artificial Sequence encoding a fusion protein
      of human serum albumin and interferon(alpha2a)

<400> SEQUENCE: 16
gatgcacaca aatcagaagt tgctcataga ttcaaggacc tcggagaaga gaacttcaag         60
gctcttgtcc ttatcgcttt cgctcaatac cttcagcaat gtccttttga ggaccacgtt        120
aagttggtga acgaagttac cgagttcgct aaaacttgcg tagctgacga atctgctgag        180
aactgtgaca agtcacttca cactcttttt ggtgacaagc tttgtactgt cgctaccctt        240
cgtgaaacct acggcgaaat ggccgattgc tgtgctaagc aggaacctga agaaacgaa         300 tgtttcttgc agcacaagga cgataacccc aatcttcctc gtttggttcg tcctgaggtc        360
gacgttatgt gcaccgcttt tcatgacaac gaagagactt tcttaaagaa ataccttac         420 gaaatcgctc gtcgtcaccc atacttctac gctccagagc tgttgttctt cgcaaagaga        480
tataaggctg cttcactga gtgttgccaa gctgctgaca aggcagcttg tctattgcct         540
aagcttgacg aattgcgaga tgagggtaaa gcatcttccg ccaagcagag attgaaatgc        600
gcttccttgc agaagtttgg tgagcgagct ttcaaagcct gggccgtggc taggttgagc        660
caacgttttc ctaaagctga gttcgctgaa gtttctaagt tggttactga tcttactaag        720
gtgcacactg aatgttgcca cggtgacctt ctggagtgtg ctgatgaccg tgcagatttg        780
gctaagtata tttgtgaaaa ccaagattct atttcttcta aactaaagga atgttgtgaa        840
aagccacttc ttgagaaaag tcactgtatc gctgaggtgg agaacgacga gatgccagct        900
gaccttccta gcctggctgc tgatttcgtt gaatctaagg acgtatgcaa gaattacgca        960
gaggccaagg atgttttcct tggcatgttt ttgtacgagt acgctagaag acaccctgac       1020
tactccgtag ttctcttgct gagggttggca aagacctacg agactaccct agagaagtgt       1080
tgcgccgcag ctgatcctca cgagtgttat gctaaagttt ttgatgagtt taaacctttg       1140
gttgaggagc acaaaaactt gattaagcag aactgcgagc ttttcgaaca attgggggaa       1200
tacaagttcc aaaatgcctt gctagtcagg tacaccaaaa aggtccctca ggtcagcacc       1260
ccaaccttag tcgaggtgtc cagaaatttg ggcaaagttg ttctaaatg ttgcaagcac        1320 ccagaagcta agaggatgcc atgtgccgaa gactaccttt ccgtcgttct gaaccaactc       1380
tgtgttttgc acgaaaagac tccagtctca gaccgtgtca cgaaatgttg taccgagtct       1440
ctggttaaca aagaccttg tttctctgct ttggaagttg acgaaactta cgtcccaaag       1500
gagttcaacg cggagacttt caccttccac gccgacattt gtacactttc cgagaaggaa       1560
agacaaatca gaagcaaac cgcactagtt gaattggtta acataagcc taaggctacc         1620 aaagaacaat tgaaagcagt tatggatgat tttgcggctt tcgtggaaaa gtgttgtaag       1680
gctgatgaca aggaaacctg ttttgccgaa gaaggtaaga agttagtcgc cgcctctcag       1740
gctgctcttg gactgtgcga cttgcctcaa acacactcat tggttcaag acgtacttta        1800 atgcttctcg ctcagatgag aaagattcc ctgttctctt gtctaaagga ccgtcacgac        1860
```

```
ttcggttttc cacaagagga atttggaaac caattccaaa aagctgagac tattcccgtt    1920
ttacacgaaa tgatccaaca gattttcaac cttttctcta ctaaggattc ttccgctgca    1980
tgggacgaaa ctttgctcga caaattctac accgaactttaccaacagct taatgaccta    2040 gaagcctgcg tgatacaggg cgtcggtgtc acagaaacgc cattgatgaa ggaggatagc    2100
atcttggccg tgcgtaagta tttccaaaga attactttgt accttaagga aaagaaatac    2160
tctccttgtg cttgggaagt agtcagagct gaaattatga gatccttttc cctttctact    2220
aacttgcaag agtccttaag atcgaaggaa taa                                 2253
```

<210> SEQ ID NO 17
<211> LENGTH: 19
<212> TYPE: DNA
<213> ORGANISM: Artificial Sequence
<220> FEATURE:
<223> OTHER INFORMATION: Synthesized Artificial Sequence

<400> SEQUENCE: 17

```
cagaaacgga aggaggttg                                                   19
```

<210> SEQ ID NO 18
<211> LENGTH: 20
<212> TYPE: DNA
<213> ORGANISM: Artificial Sequence
<220> FEATURE:
<223> OTHER INFORMATION: Synthesized Artificial Sequence

<400> SEQUENCE: 18

```
ctgacttcag ctccagattg                                                  20
```

<210> SEQ ID NO 19
<211> LENGTH: 18
<212> TYPE: DNA
<213> ORGANISM: Artificial Sequence
<220> FEATURE:
<223> OTHER INFORMATION: Synthesized Artificial Sequence

<400> SEQUENCE: 19

```
gtactccacc tggtggtc                                                    18
```

<210> SEQ ID NO 20
<211> LENGTH: 654
<212> TYPE: DNA
<213> ORGANISM: Artificial Sequence
<220> FEATURE:
<223> OTHER INFORMATION: Artificial Sequence encoding a human antibody
      fragment

<400> SEQUENCE: 20

```
caatccgtcc tgacccaacc tccttccgtt tctgctgctc ctggtcaaaa ggtcaccatt      60
tcctgttctg gatcttcatc taacattgga agaattacg tttcctggta ccaacagtta     120
ccaggtgctg cacctaagtt acttatcttt gatgacactc aaagaccatc cggaatccca     180
gacagattct ctggttctaa gtctggtact ccgcaacccc tggccatcac cggattgcag     240
actggtgatg aggccgacta ctattgcggt acttgggact tctctctgtc tactggtcaa     300
cttttcggag gtggtaccaa attgaccgtt ttgggtcagc ctaaggctgc tccatctgtt     360 actcttttc ctccatcttc agaggaattg caggccaaca aggctactct tgtttgtttg     420
atttctgact ctaccctggt gcagtcact gtggcatgga agctgattc atctccagtc     480 aaagctggtg tggagactac cactccatct aagcaatcta acaacaaata cgcagcttca     540
```

```
tcctatttgt ctttgacccc agagcagtgg aagtcccacc gttcatactc ctgtcaagtt    600
acccatgagg gttctactgt tgaaaagact atggcccacg ctgaatgctc ctaa          654

<210> SEQ ID NO 21
<211> LENGTH: 687
<212> TYPE: DNA
<213> ORGANISM: Artificial Sequence
<220> FEATURE:
<223> OTHER INFORMATION: Artificial Sequence encoding a human antibody
      fragment

<400> SEQUENCE: 21
caagtgcaag ttgttcaatc tggagctgaa gtcagaaagc caggagcttc tgttaaagtg     60
tcatgtaaag tttctggttt cactttgacc ggtttatcca ttcactgggt tagacaagca    120
cctggtaaag gtttggaatg gatgggtgga tttggtccag aggaaaatga gattatctat    180
gctcaaaagt tccagggtag agtctccatg accgaggaca cttccaccaa tactgcatac    240
atggaattgt cctctcttag atcagaagat actgctgtct actattgtgc tactggtggt    300
aactattaca acttgtggac tggttactac cctttagctt actggggtca gggtactctg    360
gttactgtct cttcagcctc tactaaggga ccatctgttt ttccacttgc tccttcctct    420
aagtccacct ctggtggaac cgctgcactg ggttgtttgg tcaaggatta cttcccagag    480
ccagttaccg tgtcttggaa ctctggtgcc cttacttctg gtgtccatac cttcccagcc    540
gttttgcagt catctggact ttactccctt tcctctgttg tcactgttcc ttcctcctct    600
ttgggaactc aaacctacat ctgcaacgtt aaccacaagc cttctaacac caaggttgac    660
aaaaaggtgg agcctaagtc ttgctaa                                        687
```

PROTEIN EXPRESSION

REFERENCE TO A SEQUENCE LISTING SUBMITTED ELECTRONICALLY VIA EFS-WEB

The content of the sequence listing (Name: eolf-seql.txt, Size: 26,017 bytes; and Date of Creation: Mar. 20, 2014) electronically submitted via EFS-Web is incorporated by reference in its entirety.

The present invention relates to a genetically modified yeast cell able to overexpress at least one polypeptide or protein supporting the biosynthesis of polypeptides or proteins within said cell.

Chaperones, in particular protein disulfide isomerase (PDI), are well known enzymes occurring in particular in the endoplasmic reticulum of eukaryotes. Chaperones assist the folding or unfolding and the assembly or disassembly of macromolecular structures like proteins and polypeptides within cells. PDI, for instance, is able to catalyze the formation, breakage and rearrangement of disulfide bonds between cysteine residues within proteins and polypeptides. PDI plays a crucial role in protein expression since this enzyme is responsible for the correct folding of disulfide bridges containing proteins expressed in eukaryotic cells. Many prokaryotes, including E. coli, which are regularly used in recombinant protein expression lack PDI activity.

In order to express correctly folded polypeptides and proteins comprising disulfide bonds it is suggested in the art to express next to the polypeptide or protein of interest also PDI. The co-expression of PDI in a recombinant host cell leads not only to correctly folded products but is responsible also for a higher product yield compared to cells which do not express PDI or which express PDI in a lower amount compared to those cells co-expressing PDI (see e.g. WO 94/08012). Moreover, it was found that an increased formation of PDI in eukaryotic cells naturally expressing PDI results in a significantly increased biosynthesis of a protein or polypeptide of interest, although there exist exceptions as reported in Butz J A et al. (Biotech Bioeng 84 (2003):292-304).

In WO 93/25676 it is suggested to integrate recombinant expression cassettes comprising a gene encoding PDI into the genome of a host cell, in particular of the yeast cell. The integration of such expression cassettes into the genome of yeast cells, for instance, is not trivial. In the course of the integration process it is highly probable that the expression cassette is integrated into the genome more than once and potentially at different sites. Therefore, it is not always possible to generate yeast cells having the same properties. Furthermore it is also known in the art that the expression efficiency of a nucleic acid molecule integrated into the genome of a yeast cell highly depends on the integration site. This means, that the integration of an expression cassette at one locus within a cell will most probably give different results compared to cells in which the expression cassette is integrated at another site within the genome. Yeast cells comprising such recombinant PDI expression cassettes still produce PDI whose encoding gene can be naturally found within the cell. Therefore such cells express on one side PDI from the expression cassette and on the other side the PDI natively present in the gene of the cell. This may lead to varying PDI levels within the cell in the course of cultivation processes. Moreover, production of target protein(s) can be negatively affected by over-expressing PDI from a recombinant expression cassette due to metabolic competition for transcription or translation (Butz J A et al., Biotech Bioeng 84 (2003):292-304).

A further and important disadvantage of using recombinant expression cassettes as proposed in WO 93/25676 is that it is required to co-transform the yeast cell with at least two nucleic acid constructs, one harbouring the gene encoding PDI and another one comprising at least one gene encoding the at least one protein of interest to be expressed within the host cell (Gupta C S et al., J Mol Endocrin 22 (1999):273-283). Co-transformation requires the provision of at least two different selection markers at once which in practice leads often to problems with false positive clones in the course of the clone selection. Alternatively, a serial transformation strategy could be needed, with separated transformations of e.g. first transformation of a nucleic acid construct harbouring the gene encoding PDI, and second transformation of nucleic acid construct harbouring at least one gene encoding the at least one protein of interest to be expressed within a host cell (Payne M S et al., Gene 194 (1997):179-182). Thereby, clonal variations are prone. Transformation of one nucleic acid construct harbouring both, the gene encoding PDI as well as at least one gene encoding the at least one protein of interest to be expressed within a host cell, in practice leads to the constraint of low transformation efficiencies due to the large molecular weight of the nucleic acid construct. Furthermore, difficulties arise from potential plasmid instabilities, be it in integrated or extrachromosomal form (Finnis C J A et al., Microbial Cell Factories 9 (2010):87).

Subramanian et al. (PNAS 103 (2006): 939-944) report on replacement of the promoter of pbn1 gene in order to study the consequences of a lack of transcription and consequently availability of the protein encoded by this gene. The authors found that Pbn1p is required for the degradation of lumenal proteins in the endoplasmic reticulum.

One object of the present invention is to provide means and methods which allow synthesizing a polypeptide or protein of interest in a much higher yield compared to methods known in the art.

Therefore the present invention relates to a method for producing a recombinant protein or polypeptide of interest comprising the steps of:
  providing a genetically modified yeast cell comprising
    a) a secretion cassette comprising a recombinant nucleic acid molecule encoding a protein or polypeptide of interest and
    b) at least one recombinant promoter operably linked to at least one gene encoding a polypeptide or protein supporting the biosynthesis of polypeptides or proteins within said cell, said at least one gene being located at the native genomic locus of the genetically unmodified wild-type yeast cell, wherein the naturally occurring promoter of the at least one gene encoding the biosynthesis supporting polypeptide or protein is inactivated by at least one mutation within said naturally occurring promoter,
  cultivating said genetically modified yeast cell in a culture medium under conditions that allow for expression of the protein or polypeptide of interest and the at least one gene encoding the biosynthesis supporting polypeptide or protein and
  isolating the protein or polypeptide of interest from the culture medium.

The present invention relates also to a genetically modified yeast cell comprising
  at least one recombinant promoter operably linked to at least one gene encoding a polypeptide or protein supporting the biosynthesis of polypeptides or proteins within said cell, said at least one gene being located at the native genomic locus of the genetically unmodified wild-type yeast cell, wherein the naturally occurring promoter of the at least one gene encoding the biosynthesis supporting polypeptide or protein is inactivated by at least one mutation within said naturally occurring promoter and a secretion cassette comprising a recombinant nucleic acid molecule encoding a protein or polypeptide of interest.

A further aspect of the present invention relates to a genetically modified yeast cell comprising at least one recombinant promoter operably linked to at least one gene encoding a polypeptide or protein supporting the biosynthesis of polypeptides or proteins within said cell, said at least one gene being located at the native genomic locus of the genetically unmodified wild-type yeast cell, wherein the naturally occurring promoter of the at least one gene encoding the biosynthesis supporting polypeptide or protein is inactivated by at least one mutation within said naturally occurring promoter.

Surprisingly, it turned out that cells comprising a recombinant promoter operably linked to at least one gene naturally occurring in the genome of the host cell and encoding a polypeptide or protein supporting the biosynthesis of recombinant polypeptides or proteins within said cell are not able to produce a recombinant protein or polypeptide of interest or at least to a lower extent than comparable host cells if the naturally occurring promoter is still active (at a maximum of 10%, preferably at a maximum of 5%, more preferably at a maximum of 2%, even more preferably at a maximum of at least 1%, of its native activity determined by measuring the transcribed and/or translated gene product) or at least present in full length upstream of the newly introduced promoter. Therefore it is required that the naturally occurring promoter is inactivated by mutating said promoter. Such an inactivation leads in the most preferred embodiment of the present invention to no measurable transcription and/or translation of the gene naturally linked thereto. However, the term "inactivated" includes also a residual promoter activity of a maximum of 10%, preferably at a maximum of 5%, more preferably at a maximum of 2%, even more preferably at a maximum of at least 1%, of its native activity. The promoter activity can be simply determined by measuring the transcribed gene and/or translated gene product by using methods known in the art.

According to the present invention the yeast cell may comprise one or more, preferably one, recombinant promoters operably linked to one or more naturally occurring genes encoding a polypeptide or protein supporting the biosynthesis of polypeptides or proteins within said cell. One and the same promoter can be operably linked to more than one (i.e. different) naturally occurring genes encoding a polypeptide or protein supporting the biosynthesis of polypeptides or proteins within the cell. On the other side it is also possible to provide a cell which comprises one or more naturally occurring genes encoding a polypeptide or protein supporting the biosynthesis of polypeptides or proteins to which more than one copy of one and the same promoter is operably linked thereto. This means that a yeast cell of the present invention may comprise e.g. one promoter operably linked to one gene encoding a polypeptide or protein supporting the biosynthesis of polypeptides or proteins and another promoter to another gene encoding a polypeptide or protein supporting the biosynthesis of polypeptides or proteins. Of course it would also be possible to operably linking one specific promoter to more than one gene encoding a polypeptide or protein supporting the biosynthesis of polypeptides or proteins.

A "gene encoding a polypeptide or protein supporting the biosynthesis of polypeptides or proteins" is a gene that encodes a polypeptide or protein which actively supports the recombinant and/or native expression of polypeptides and proteins within a cell. If said polypeptide or protein is not expressed or expressed in a lower extend compared to a reference cell (e.g. wild-type cell) the native and/or recombinant protein or polypeptide is either not expressed or secreted at all or to a much lower extent compared to a cell in which these expression or secretion supporting polypeptides or proteins are present within the cell in normal levels.

The term "recombinant promoter", as used herein, refers to a promoter which is not naturally occurring in the genome in the upstream region of the gene encoding a polypeptide or protein supporting the biosynthesis of recombinant polypeptides or proteins within a host cell in order to control the transcription of said gene. The recombinant promoter can be a promoter derived from the same or another yeast cell or a heterologous promoter being derived from any other source provided that the recombinant promoter is functional (i.e. is able to control the transcription of the gene operably linked thereto) in the host cell. Of course the term "promoter" includes also fragments of a wild-type promoter, provided that said fragments are able to control the transcription rate of a gene to which said promoter fragment is operably linked.

By "native genomic locus" a naturally occurring genomic sequence is intended.

The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the encoding sequence.

As used herein, the term "cassette" refers to a nucleotide sequence capable of expressing a particular gene if said gene is inserted so as to be operably linked to one or more regulatory sequences present in the nucleotide sequence. Thus, for example, the expression cassette may comprise a heterologous gene which is desired to be expressed through glucose induction. The expression cassettes of the present invention are therefore useful for promoting expression of any number of heterologous genes upon induction. Furthermore, the cassette of the present invention contains a nucleic acid stretch which encodes for a signal peptide which allows the secretion of the polypeptide or protein fused thereto. Such a cassette is according to the present invention intended to be a "secretion cassette". The secretion signal sequence may be any sequence that is used as the secretion signal in the yeast cell or is conventionally known in the art (e.g. alpha-factor or alpha mating factor"). According to a particular preferred embodiment of the present invention said at least one recombinant promoter enables the genetically modified yeast cell to produce at least 100% more, preferably at least 200% more, more preferably at least 300% more, of the polypeptide or protein supporting the biosynthesis of polypeptides or proteins compared to the genetically unmodified wild-type yeast cell.

The at least one recombinant promoter operably linked to at least one gene encoding a polypeptide or protein supporting the biosynthesis of polypeptides or proteins within said cell can be an inducible or constitutive promoter (in yeast cells). Respective promoters are well known in the art. Suitable promoters which can be used according to the present invention allow the cell to produce at least 100% (200%, 300%, 400%, 500%, . . . ) more of said polypeptide or protein as the wild-type yeast cell comprising the naturally occurring promoter associated to the at least one gene encoding a polypeptide or protein supporting the biosynthesis of polypeptides or proteins within said cell.

Methods to identify the expression rate of a specific protein or polypeptide within the cell are well known in the art and may involve disruption of the cells and antibodies binding specifically to said at least one protein or polypeptide.

The yeast cell of the present invention carrying the nucleic acid molecules as define above can be cultivated using conventional methods using conventional and established nutrient media. In order to produce the recombinant protein or polypeptide of interest the cells have to be cultivated "under conditions that allow for expression" of said polypeptides and proteins. This means that to the culture medium substances may be added or removed (removal of substances may occur by changing the culture medium) in order to activate the promoters operably linked to the genes encoding the polypeptide or protein supporting the biosynthesis of polypeptides or proteins and/or the protein or polypeptide of interest.

According to a preferred embodiment of the present invention the at least one gene encoding a polypeptide or protein supporting the biosynthesis of (native and/or recombinant) polypeptides or proteins within said cell is a chaperone.

"Chaperones" as used herein refers to polypeptides and proteins that assist the folding or unfolding and the assembly or disassembly of other macromolecular proteinaceous structures, but do not occur in these structures when the structures are performing their normal biological functions having completed the processes of folding and/or assembly. One major function of chaperones is to prevent both newly synthesized polypeptide chains and assembled subunits from aggregating into nonfunctional structures. "Chaperones" according to the present invention include also "protein foldases" such as protein disulfide isomerase. The chaperones of the present invention are preferably present in appropriate cellular compartments (e.g. endoplasmic reticulum (ER) and/or Golgi-apparatus and/or vesicles along the secretory pathway for secreted recombinant proteins).

Advantageously the inactivation of the wild type chaperone promoter as well as other promoters of at least one gene encoding a polypeptide or protein supporting the biosynthesis of polypeptides or proteins does not negatively affect the viability of the genetically modified yeast cell. If the inactivation of said promoter is lethal or reduces significantly the viability of the host cell, the chaperone promoter should of course not be modified in the way described herein.

"Chaperone promoter is inactivated" means that the in vivo activity of the wild type chaperone promoter is reduced to a maximum of 10%, preferably to a maximum of 5%, more preferably to a maximum of 2%, of the promoter activity of the wild type host cell. Methods to determine the promoter activity are well known in the art and may involve the use of specific marker proteins or polypeptides. However, it is particularly preferred that the wild-type chaperone promoter in the genetically modified cell of the present invention is completely inactivated, so that no promoter activity can be determined within the cell.

According to a preferred embodiment of the present invention the chaperone is selected from the group consisting of protein disulfide isomerase, binding protein Kar2/BiP and calnexin, whereby disulfide isomerase is particularly preferred.

According to another preferred embodiment of the present invention the recombinant promoter is an inducible genetically modified or unmodified yeast promoter.

In order to control the expression rate of the at least one gene encoding a polypeptide or protein supporting the biosynthesis of polypeptides or proteins, preferably protein disulfide isomerase, within the yeast cell it is advantageous to use an inducible promoter. It is of course possible to use any kind of promoter provided that the promoter is able to control the transcription of a gene operably linked thereto in a yeast cell. However, it is particularly preferred to use a promoter which is derived from a yeast cell.

The promoter used in the present invention may be an unmodified wild-type promoter which is directly derived from a respective source. Of course it is also possible to use promoters which comprise at least one mutation. Such promoters have the advantage that the introduction of mutations within the promoter allows to modify the in vivo transcriptional regulation activity resulting in a promoter having lower or higher activity compared to the respective wild-type promoter at specific points of cultivation. "Genetically modified promoter", as used herein, refers therefore to a promoter that has been modified by any suitable conventional or molecular biology method well known in the art, by DNA techniques, such as by site directed mutagenesis, deletion or insertion, or by conventional mutagenesis using chemical agents or irradiation, followed by screening or selecting for cells modified in the transcriptional mechanism (see e.g. WO 2006/089329).

Alternatively it is of course also possible to use promoters which act constitutively in the host cell. In some cases the constitutive expression of a chaperone using a recombinant promoter leads also to an increased formation of a protein or polypeptide of interest. Constitutive promoters for yeast cells are well known in the art.

According to another preferred embodiment of the present invention the yeast promoter to be operably linked to the at least one gene encoding a polypeptide or protein supporting the biosynthesis of polypeptides or proteins within said cell, preferably PDI, is selected from the group consisting of AOX1 promoter, GAL1 promoter, PGK promoter, FDH promoter, FLD promoter, ADH promoter and HIS4 promoter.

Particularly preferred is the use of an unmutated or mutated AOX1 promoter.

Mutations within a promoter, in particular of an inducible promoter, may result in a genetically modified promoter exhibiting altered properties compared to the wild-type promoter. Specific mutations may lead to a promoter showing under inducing conditions higher activity (i.e. the transcription rate of the gene operably linked thereto is increased) than unmodified promoters. Of course, it is also possible to provide mutations which show the opposite effect. Particularly preferred parts of the AOX1 promoter to be genetically modified are shown in Ivan M et al. (Biotechnol Bioeng 2006; 93: 771-778) and in particular in WO 2006/089329 (incorporated herein by reference).

Preferred variants of the wild type AOX1 promoter (SEQ ID No. 1) to be used in the present invention comprise at least one mutation (e.g. deletion, insertion, nucleotide exchange) within the sites and nucleotide ranges selected from the group consisting of:

a) a transcription factor binding site (TFBS), b) nucleotides 170 to 235, nucleotides 170 to 191, nucleotides 192 to 213, nucleotides 192 to 210, nucleotides 207 to 209, nucleotides 214 to 235, nucleotides 304 to 350, nucleotides 364 to 393, nucleotides 434 to 508, nucleotides 509 to 551, nucleotides 552 to 560, nucleotides 585 to 617, nucleotides 621 to 660, nucleotides 625 to 683, nucleotides 736 to 741, nucleotides 737 to 738, nucleotides 726 to 755, nucleotides 784 to 800 or nucleotides 823 to 861 of Seq ID No. 1, and combinations thereof, wherein the promoter stretches comprising the above mentioned transcription factor binding sites (TFBS) comprise Hap1 nucleotides 54 to 58 of Seq ID No. 1, Hsf nucleotides 142 to 149 and 517 to 524 of Seq ID No. 1, Hap234 nucleotides 196 to 200, 206 to 210 and 668 to 672 of Seq ID No. 1, abaA nucleotides 219 to 224 of Seq ID No. 1, Stre nucleotides 281 to 285 of Seq ID No. 1, Rap1 nucleotides 335 to 339 of Seq ID No. 1, Adr1 nucleotides 371 to 377 of Seq ID No. 1, Mat1MC nucleotides 683 to 687 of Seq ID No. 1, Gcr1 nucleotides 702 to 706 of Seq ID No. 1 and QA-1F nucleotides 747 to 761 of Seq ID No. 1.

activity, because structural features and/or recognition/binding sites for e.g. transcription factors are affected by said mutations. However, these changes may lead to an increased or decreased activity of the promoter compared to the wild type promoter.

```
Seq ID No. 1: AOX1 promoter of Pichia pastoris
ggtaccagatctaacatccaaagacgaaaggttgaatgaaaccttttgccatccgacatccac aggtccattctcacacataagtgccaaacgcaacaggaggggatacactagcagcagaccgttg caaacgcaggacctccactcctcttctcctcaacacccacttttgccatcgaaaaaccagccca gttattgggcttgattggagctcgctcattccaattccttctattaggctactaacaccatgac tttattagcctgtctatcctggcccccctggcgaggttcatgtttgtttatttccgaatgcaac aagctccgcattacacccgaacatcactccagatgagggctttctgagtgtggggtcaaatagt ttcatgttccccaaatggcccaaaactgacagtttaaacgctgtcttggaacctaatatgacaa aagcgtgatctcatccaagatgaactaagtttggttcgttgaaatgctaacggccagttggtca aaaagaaacttccaaaagtcggcataccgtttgtcttgtttggtattgattgacgaatgctcaa aaataatctcattaatgcttagcgcagtctctctatcgcttctgaacccggtgcacctgtgcc gaaacgcaaatggggaaacacccgcttttggatgattatgcattgtctccacattgtatgctt ccaagattctggtgggaatactgctgatagcctaacgttcatgatcaaaatttaactgttctaa cccctacttgacagcaatatataaacagaaggaagctgccctgtcttaaacctttttttttatc atcattattagcttactttcataattgcgactggttccaattgacaagcttttgattttaacga cttttaacgacaacttgagaagatcaaaaaacaactaattattgaaagaattcaacc
```

The yeast promoter is preferably an AOX1 promoter comprising at least one mutation within nucleotides 170 to 235 or 694 to 723 or 694 to 723 and 737 to 738 of SEQ ID No. 1.

An AOX1 promoter comprising at least one mutation within nucleotides 170 to 235 of SEQ ID No. 1 shows a much higher expression rate under methanol inducing conditions compared to the wild-type AOX1 promoter. An AOX1 promoter comprising at least one mutation within nucleotides 694 to 723 or 694 to 723 and 737 to 738 of SEQ ID No. 1 shows a much higher expression rate under derepression conditions compared to the wildtype AOX1 promoter (see e.g. WO 2006/089329).

The mutation of the AOX1 promoter is preferably a deletion, a substitution, an insertion, an inversion and/or a multiplication within the aforementioned nucleotides of the wild-type AOX1 promoter.

In order to modify the characteristics of the wild type AOX1 promoter of Pichia pastoris several mutation types are possible. The promoter stretches comprising the above mentioned regions as well as one or more of the transcription factor binding sites (TFBS) Hap1 comprising nucleotides 54 to 58 of Seq ID No. 1, Hsf nucleotides 142 to 149 and 517 to 524 of Seq ID No. 1, Hap234 nucleotides 196 to 200, 206 to 210 and 668 to 672 of Seq ID No. 1, abaA nucleotides 219 to 224 of Seq ID No. 1, Stre nucleotides 281 to 285 of Seq ID No. 1, Rap1 nucleotides 335 to 339 of Seq ID No. 1, Adr1 nucleotides 371 to 377 of Seq ID No. 1, Mat1MC nucleotides 683 to 687 of Seq ID No. 1, Gcr1 nucleotides 702 to 706 of Seq ID No. 1 and QA-1F nucleotides 747 to 761 of Seq ID No. 1 may be partially or completely deleted, partially or completely substituted with other nucleotides or nucleic acid sequences, disrupted by insertion of single nucleotides or nucleic acid sequences, inverted partially or completely or multiplied. All these mutations lead to a change in promoter In a special embodiment of the present invention the yeast cell is selected from the following group consisting of Pichia species, Hansenula species such as Hansenula polymorpha, Saccharomyces species, Schizosaccharomyces species, Yarrowia species such as Yarrowia lipolytica, Kluyveromyces species and Aspergillus species.

According to a particularly preferred embodiment of the present invention the yeast cell is a methylotrophic yeast cell, preferably selected from the group consisting of a yeast of the genus of Pichia, preferably Pichia pastoris, Candida boidinii and Hansenula polymorpha.

The at least one mutation of the naturally occurring chaperone promoter of the at least one gene encoding the biosynthesis supporting polypeptide or protein is preferably a deletion.

The inactivation of the naturally occurring promoter within the host cell can occur in various ways. For instance, it would be possible to introduce point mutations within said promoter. Suitable mutations can easily be identified by introducing potential mutations within said promoter and then test in vivo the activity of the promoter. However, the most efficient way to inactivate a promoter within the host cell is a deletion of at least a part of the promoter. Therefore it is particularly preferred to delete at least in part the promoter naturally occurring in the host cell. The deletion may occur in any part of the promoter, whereby it is particularly preferred to delete those parts which are found next to the start codon of the gene encoding the biosynthesis supporting polypeptide or protein (i.e. 5' region of said gene).

According to a particularly preferred embodiment of the present invention at least 50 nucleotides, preferably at least 100 nucleotides, more preferably at least 200 nucleotides, even more preferably at least 500 nucleotides, of the promoter of the naturally occurring at least one gene encoding a polypeptide or protein supporting the biosynthesis of polypeptides or proteins within said cell, preferably protein disulfide isomerase, is deleted.

It is particularly preferred to delete at least the first 50, preferably at least the first 100, more preferably at least the first 200, even more preferably at least the first 500, consecutive nucleotides in the upstream region of the start codon of the gene encoding the biosynthesis supporting polypeptide or protein (i.e. 5' end of said gene).

In order to express a protein or polypeptide of interest in the yeast cell said cell comprises further a nucleic acid molecule encoding a protein or polypeptide of interest operably linked to a promoter, preferably an inducible promoter.

The promoter operably linked to the gene encoding the biosynthesis supporting polypeptide or protein can be the same as the promoter operably linked to a nucleic acid molecule encoding a protein or polypeptide of interest. However, it is preferred that the at least one gene encoding the biosynthesis supporting polypeptide or protein and the gene encoding a protein or polypeptide of interest are controlled by different promoters. In this context, the term "different promoters" means that the activities of the promoters are not identical but differ from each other. Therefore it would be possible to use modified and non-modified promoters derived from the same wild-type promoter exhibiting altered effects when the cell comprising said promoters is cultivated. This allows regulating independently the expression of the biosynthesis supporting polypeptide or protein and a protein or polypeptide of interest. The independent regulation of the expression of the biosynthesis supporting polypeptide or protein and a protein or polypeptide of interest is advantageous because it allows optimizing the expression rates of the protein or polypeptide of interest.

According to a preferred embodiment of the present invention the nucleic acid molecule encoding a protein or polypeptide of interest is part of a vector or integrated into the genome.

The nucleic acid molecule encoding the protein or polypeptide of interest can be part of a vector or integrated into genome by using respective means and methods which are well known to the person skilled in the art. The means and methods to be used depend also on the host cell and have to be selected accordingly (see e.g. "*Pichia* Protocols", Cregg J M, Humana Press; 2nd edition (Aug. 8, 2007).

The nucleic acid molecule of the present invention comprises also signal sequences which allow the secretion of the protein or polypeptide of interest into the supernatant of the culture medium in which the cells are cultivated.

The term "signal sequence" as used herein refers to a segment which directs the secretion of the biologically active molecule. The signal sequence used in the present invention may be a polynucleotide which encodes an amino acid sequence initiating transport of a protein across the membrane of the endoplasmic reticulum (ER). The non-limiting examples of the signal sequence are MFa (mating factor α signal sequence), K₁ killer toxin signal, invertase secretion signal peptide, killer toxin of Kluyveromyces lactis signal sequence, killer toxin of *Pichia acaciae* signal sequence, killer toxin of Hanseniaspora uvarum signal sequence, and killer toxin of *Pichia* (*Hansenula*) *anomala* signal sequence. The preferred signal sequence of the subject invention is MFα (mating factor α signal sequence). Preferably, for a correct folding and translocation of a target protein, MFa signal peptide is introduced. MFα is the pre-pro region from α-factor, and encodes a protein having 165 amino acids, pre-pro-α-factor, which comprises a signal sequence of 19 amino acids (the pre region) and a pro region, followed by four tandem repeats of the mature 13 amino acid α-factor sequence. In a particularly preferred embodiment the signal sequence comprises or consists of the following amino acid sequence (SEQ ID No. 11):

MRFPSIFTAVLFAASSALAAPVNTTTEDETAQIPAEAVIGYSDLEGDFD

VAVLPFSNSTNNGLLFINTTIASIAAKEEGVSLEKREAEA

The nucleic acid encoding said signal sequence has an identity of at least 95%, preferably of at least 98%, even more preferably of 100%, to the following nucleotide sequence (SEQ ID No. 12):

```
atgagattcccatctattttcaccgctgtcttgttcgctgcctcctctgcattggctgcccctg ttaacactaccactgaagacgagactgctcaaattccagctgaagcagttatcggttactctac cttgagggtgatttcgacgtcgctgttttgccttctctaactccactaacaacggtttgttgt tcattaacaccactatcgcttccattgctgctaaggaagagggtgtctctctcgagaagaagag gccgaagct
```

As used herein, the term "vector" is understood to mean any nucleic acid molecule including a nucleotide sequence competent to be incorporated into a host cell and integrated into the host cell genome, or to replicate autonomously as an episomal DNA. Such vectors include linear nucleic acids, plasmids, phagemids, cosmids, RNA vectors, viral vectors and the like. Suitable expression vector may comprise a expression regulatory factors such as a promoter, start codon, stop codon, polyadenylation signal, enhancer and selection markers.

The transformation of the nucleic acid molecules of the present invention into the yeast cell may be conducted by known methods in the art, which may be selected suitably depending on host cells. These methods include, but are not limited to, electroporation, protoplast fusion method, calcium phosphate precipitation and calcium chloride precipitation, agitation with silicon carbide fiber, and PEG-, dextran sulfate- and lipofectaminemediated transformation.

Another aspect of the present invention relates to the use of cells according to the present invention for producing a recombinant protein or polypeptide of interest.

Another aspect of the present invention relates to a method for producing at least one recombinant protein or polypeptide in a host cell of the present invention, wherein said host cell comprises at least one gene encoding the at least one recombinant protein or polypeptide, wherein the expression of at least one gene encoding a polypeptide or protein supporting the biosynthesis of recombinant or native polypeptides or proteins or chaperone naturally occurring in said host cell is increased compared to a wild-type host cell.

Yet another aspect of the present invention relates to a method for producing a recombinant or native protein or polypeptide comprising the step of cultivating a cell according to the present invention.

Methods for producing recombinant proteins or polypeptides are well known in the art. The genetically modified yeast cell according to the present invention is particularly suited to express such proteins and polypeptides because it allows to control expression rate of at least one gene encoding a polypeptide or protein supporting the biosynthesis of recombinant polypeptides or proteins, preferably chaperone, more preferably PDI, as well as proteins and polypeptides of interest in a much more efficient way. In particular it is possible to control the expression rate of at least one chaperone, preferably PDI, in various stages of cultivation and consequently to determine the point in time when the level of the at least one chaperone within the cell reaches a predetermined amount.

The method of the present invention can also comprise a step of isolating the protein or polypeptide of interest from the supernatant of the culture medium if the protein or polypeptide is secreted from the cell.

The cells of the present invention can be cultivated with any known cultivation method such as batch culture, continuous culture and fed-batch culture. Culture conditions suitable for selected yeast strains may be easily adjusted by those skilled in the art. Typically, a medium used should contain all nutrients essential for the growth and survival of cells.

The present invention is further illustrated in the following figures and examples, however, without being restricted thereto.

Figure 7:
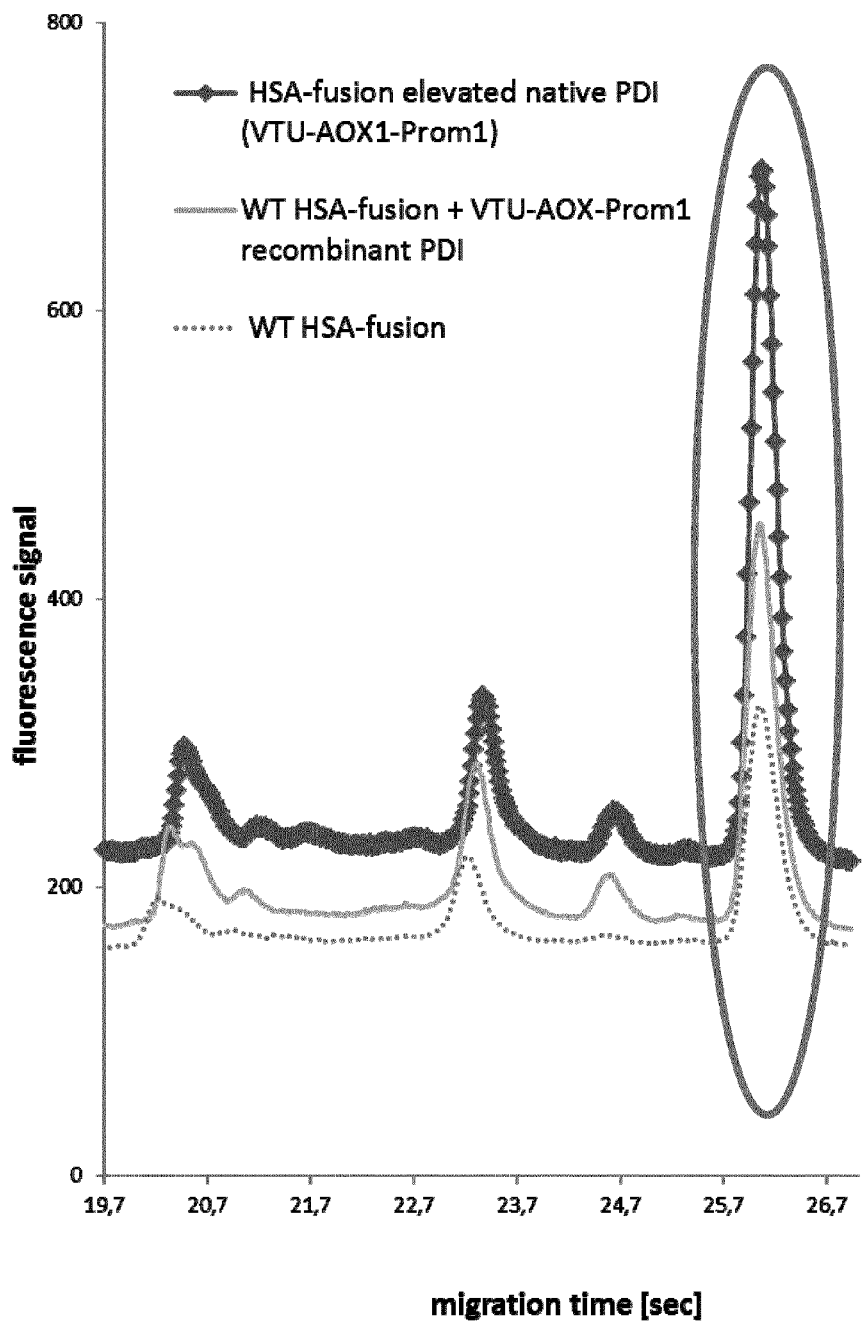

FIG. 7 shows an electropherogram overlay (GXII, Caliper Life Sciences, USA) of (directly applied) supernatant of HSAInterferon(alpha2a)-expressing strains CBS7435 muts (dotted line), CBS7435 muts strain co-expressing recombinant protein disulfide isomerase (present in 1 copy; the same promoter was used as in the CBS7435 muts PDI platform strain) (full line), and CBS7435 muts PDI platform strain (full line with diamonds), respectively.

Figure 8:
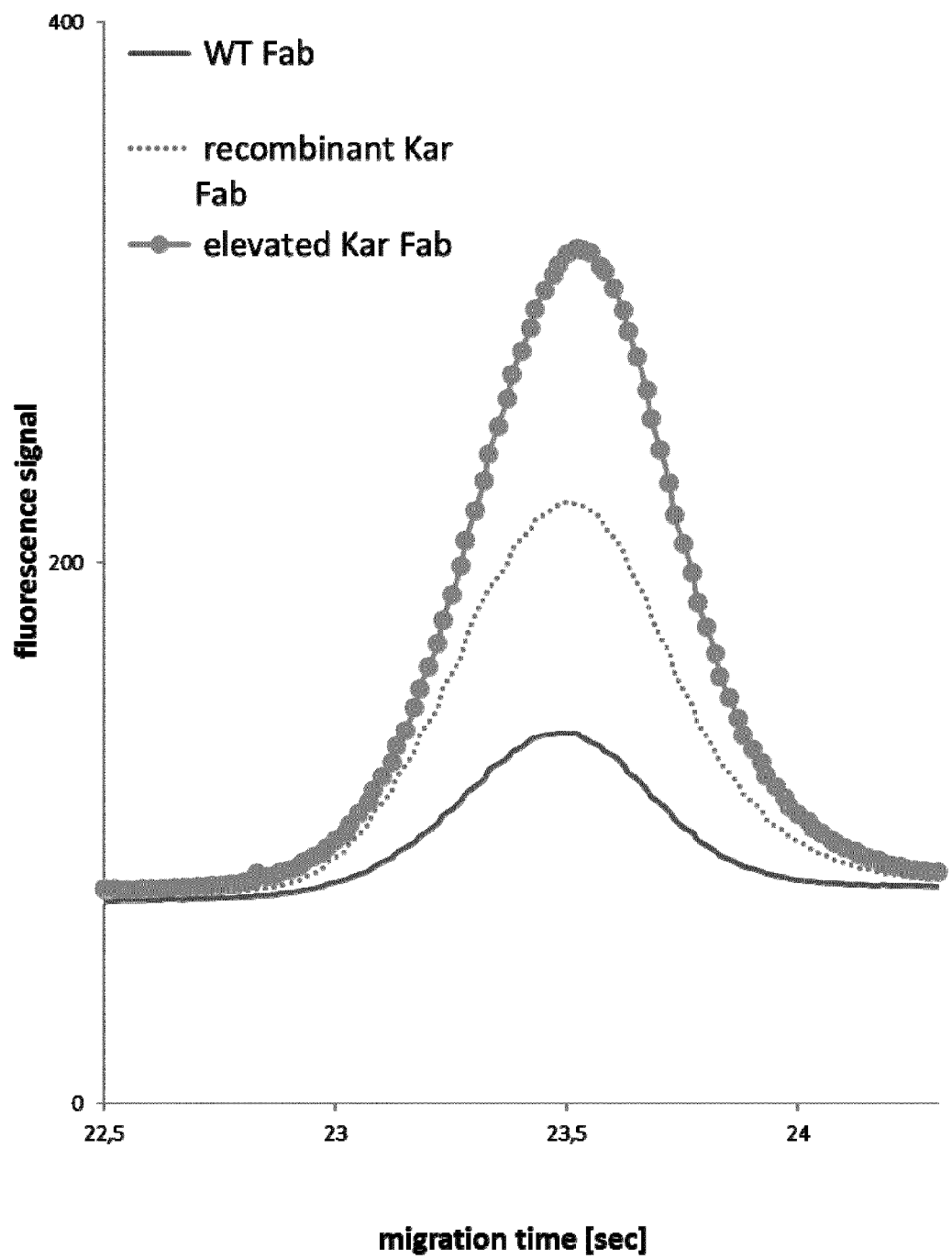

FIG. 8 shows an electropherogram overlay (GXII, Caliper Life Sciences, USA) of (directly applied) supernatant of Fabexpressing strains CBS7435 muts (full line), CBS7435 muts strain co-expressing recombinant Kar2 (present in 1 copy; the same promoter was used as in the CBS7435 muts Kar2 platform strain) (dotted line), and CBS7435 muts Kar2 platform strain (full line with rings), respectively.

EXAMPLES

Strategy

The transformed DNA construct used in the following specific examples consists of the first 700-1000 bp of the homologous promoter and a strongly regulated, specifically mutated AOX1 promoter driving the expression of Flp recombinase, followed by a transcription terminator and a resistance marker cassette, further followed by a differently regulated, specifically mutated AOX1 promoter and the first 500-1000 bp of the homologous gene. The recombinase recognition sites are placed after the first 100-300 bp of the homologous promoter (based on the assumption that the native PDI promoter may consist of approximately 1000 bp), and directly upstream of the second specific AOX1 promoter (and downstream of the restriction marker cassette).

After the genomic insertion of the transformation construct in the envisaged locus (which is predetermined by the homologous flanking regions), colonies are subjected to methanol containing media in order to induce transcription of the recombinase gene regulated by the strong inducible promoter upstream. Flp recombinase acts on the Flp recombinase recognition sites and thereby excises most of the homologous promoter, the strong inducible AOX1 promoter variant as well as the whole resistance marker cassette, leaving behind residual fractions of the homologous promoter and the differently regulated, specifically mutated AOX1 promoter driving the homologous gene of interest.

For the verification of a significant increase of PDI gene transcript levels with the strategy described above, the synthetic genes for human serum transferrin as well as the mutated variant without N-glycosylation motifs transferrin-non-glycosylated were ideal model proteins: without the co-expression of PDI from a recombinant expression cassette, both proteins cannot be secreted. The reason for this is most probably the immense number of 19 disulfide bonds to be formed for an intact protein that would be amenable for secretion, which cannot be sufficiently catalyzed by the natively occurring ERresident PDI proteins. Apparently, upon supply of additional enzymes by heterologous overexpression, the post-translational modification of transferrin and transferrin-non-glycosylated in the ER works to an extent that allows for secretion of correctly folded proteins.

Strains

Standard molecular biology procedures were performed according to Ausubel, F. M., et al. (2003) Current Protocols in Molecular Biology; John Wiley & Sons, New York, US).

*E. coli* DH5α (NEB, USA) was used for all *E. coli* cloning experiments.

*Pichia pastoris* strain CBS7435 with muts phenotype (Aaox1 genotype) was used as host for all yeast experiments (see e.g. Cregg and Madden in Stewart, Russell, Klein and Hiebsch (Eds) Biological Research on Industrial Yeast, vol II (1987), CRC Press, pp 1-18).

Chemicals and Media

Unless otherwise stated explicitly, all chemicals were purchased from Carl Roth GmbH (Germany), and Becton, Dickinson and Company (USA), respectively. Sterile water was purchased from Fresenius Kabi (Austria).

Unless specifically mentioned, all culture media and ingredients were prepared according to the protocol from the *Pichia* protein expression Kit (Invitrogen, USA).

Transformation of *P. pastoris*, *Pichia* Growth Conditions and selection for positive clones

*P. pastoris* was transformed using the standard electroporation protocol according to the "*Pichia* Expression Kit" (Invitrogen). Plasmid DNA (1-10 µg) was linearized using a restriction enzyme, e.g. BglII or SadI (both purchased from NEB, USA) for addition of the expression plasmid into the genome of *P. pastoris* and desalted via dialysis using nitrocellulose filters (0.0025 µm, Millipore, USA) against sterile water for 60 min at room temperature.

After transformation, aliquots of 100 μl were plated on YPD agar-plates supplemented with 100 μg/ml Zeocin and incubated for 2 days at 30° C.

The presence of the expression cassette in the genome of *P. pastoris* was confirmed by colony PCR. Zeocin-resistant clones were replated on non-selective media for colony PCR analysis. A single colony was resuspended in 100 μl sterile water, heated to 95° C. for 5 minutes and centrifuged at top speed in a tabletop centrifuge for 1 min. 10 μl of the supernatants served as template for a 50 μl reaction, containing 0.2 mM dNTPs, 1× reaction buffer (Qiagen, Germany), 1.2 U HotStar Taq polymerase (Qiagen), 200 nM each of the primers PPDI5_for (5'-ccaaaaccaggtgtgtcaatc-3') and PDIgene rev (5'-cgactggtctgagtgctagg-3'). The following program was used for PCR: 15 min at 95° C., 30 cycles with 30 sec at 95° C., 1 min at 61° C. and 3.5 min at 72° C., followed by a final extension step of 10 min at 72° C. The identity of the resulting PCR products was verified by DNA sequencing.

Yeast cultures were either grown in YPD medium (1% w/v yeast extract, 2% w/v peptone and 2% w/v glucose), minimal dextrose (MD) medium (1.34% Yeast Nitrogen Base YNB, 4×10$^{-5}$% biotin and 1% glucose), minimal methanol (MM) medium (1.34% YNB, 4×10-5% biotin and 0.5% methanol), buffered MD (BMD) medium (containing 200 mM sodium phosphate buffer pH 6.0) or buffered MM media with doubled (BMM2 containing 1% methanol) or ten-fold (BMM10 containing 5% methanol) concentration of methanol compared to MM, according to (Weis et al, FEMS YR 2004). Media for plates were solidified by addition of agar to 1.5% w/v.

Scale-Up

*Pichia pastoris* fermentations were carried out similar to the protocols described in Cino, J. High Yield Protein Production from *Pichia pastoris* Yeast: A Protocol for Benchtop Fermentation, New Brunswick Scientific, Edison, N.J. At the end of the glycerol feed, a methanol feed was started aiming at keeping the methanol concentration (off-line methanol analysis) around 1% by adjusting the feed rate. Alternatively, instead of feeding methanol, glycerol was fed for the whole process time at the same rate as in the classical glycerol fed-batch period of a methanol-induced fermentation. The pH-value was set at 5.5 and controlled by ammonia. Dissolved oxygen was kept above 30%, primarily controlled by stirrer speed, and backed up by aeration rate. The temperature was set to 20-28° C. Cell dry weights were determined as described in Whittaker, M. M. and Whittaker, J. M. (2000) Protein, Expr. Purif. 20, 105-111.

Determination of Secreted Target Protein

After cultivation in microscale or bioreactors, respectively, supernatant samples (obtained by separating the cells by centrifugation) were analyzed by microfluidic capillary electrophoresis (GXII, Caliper Life Sciences, USA) according to the instructions from the manufacturer. Comparison of target protein peaks to internal as well as external standards resulted in target protein yields in the culture supernatant.

Example 1

Figure 1:
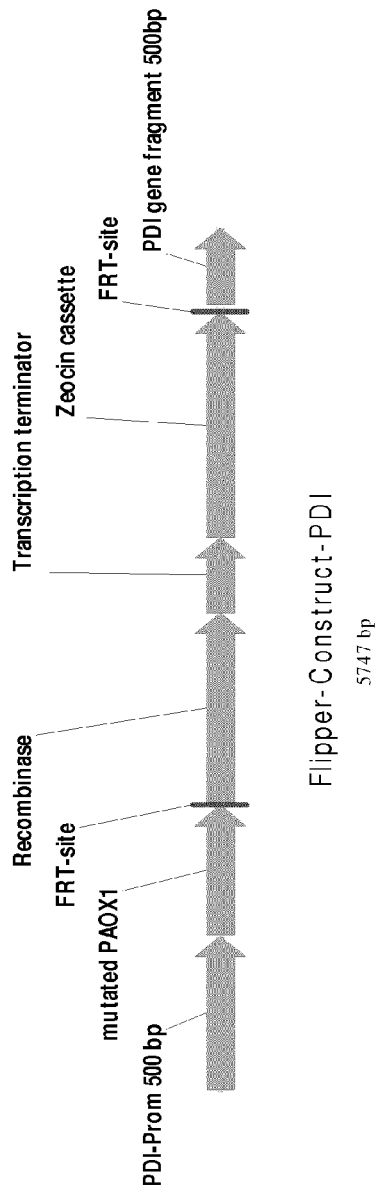
FIG. 1 shows a plasmid map of "Flipper construct" for promoter integration cassette of specifically mutated AOX1 promoter between native Protein Disulfide Isomerase (PDI) promoter and PDI gene.

Construction of Promoter Co-Integration Cassette of a Specifically Mutated AOX1 Promoter Between the Native Protein Disulfide Isomerase (PDI) Promoter and the PDI Gene The transformed DNA construct consists of the first 500 bp (from 3' end) of the homologous PDI promoter (based on the assumption that the native PDI promoter may consist of approximately 1000 bp), and a specifically regulated, mutated AOX1 promoter (WO 2006/089329; derived from SEQ ID No. 1) driving the expression of Flp recombinase, followed by CYC1 transcription terminator and a Zeocin resistance cassette (functional in *E. coli* by EM72 promoter, and in *P. pastoris* by ILV5 promoter and AOD transcription terminator), further followed by the first 500 bp of the homologous PDI gene. The recombinase recognition sites are placed after the specific AOX1 promoter, and directly upstream of the homologous PDI gene (FIG. 1). This DNA fragment was ordered as synthetically generated DNA with DNA2.0 (Menlo Park, USA).

Example 2

Transformation of Promoter Integration Construct into CBS7435 Mots, Confirmation of Genomic Constellation, Propagation on Methanol Media and Cassette Excision and Confirmation After transformation and selection on agar-plates, 20 colonies were confirmed by colony PCR to carry the integrated transformation cassette in the correct genomic orientation.

Figure 2:
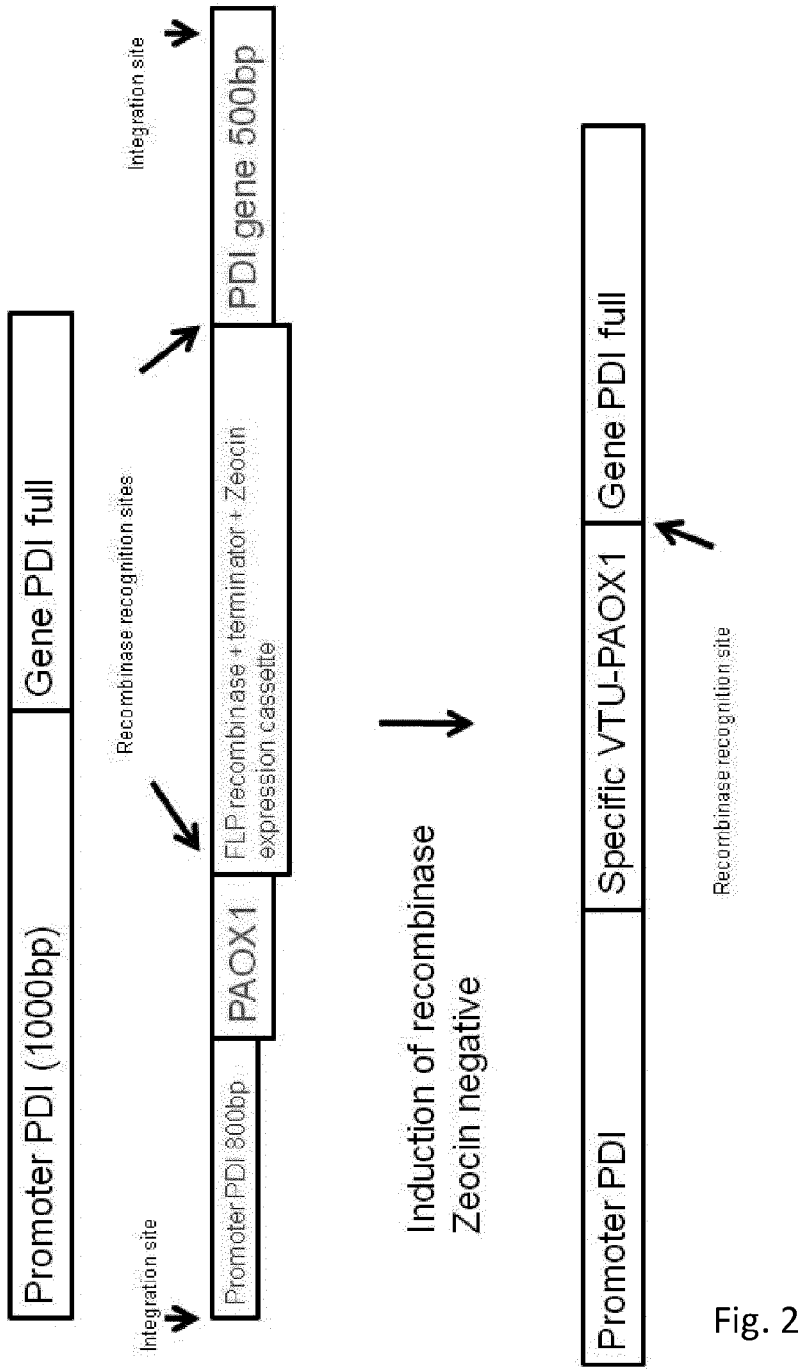
FIG. 2 shows a graphic chart of promoter integration strategy for PDI promoter.

Clones were transferred to minimal methanol agar plates for 5 days (until large single colonies are formed), in total 3 consecutive times. Thereafter, excision of the DNA region between the FRT sites (most part of the homologous promoter region, strong inducible AOX1 promoter and Flp recombinase, resistance marker cassette) was checked by counter-restreaking on YPhyD plates containing selection marker (Zeocin): positive clones, i.e. those where excision took place, were not able to grow on these plates. Colony PCR proved the occurrence of homologous PDI promoter upstream of specifically mutated AOX1 promoter, directly followed by the remaining FRT site and the (intact) PDI gene (FIG. 2, SEQ ID No. 2).

SEQ ID No. 2: sequence obtained for genomic PDI locus
Bold: native PDI promoter region (1000 bp upstream of native PDI gene in unmodified strain)
Italic: mutated AOX1 promoter
Regular: native PDI gene (first 892 bases) with 5' kozak sequence
Subscript: FRT site

```
aagggagacatattcggctattgtttactttgcgcccacagtagcgttaagaaacattgtttgt tcgatttattgggctgttgataaattcaattgattacgttcgcatactagctatcataaactaa gcaccaccttacaccactttctcactgaagattttcgacatcaaatttctcttggatcaccatc aaccttgtgtctacatgtccttgtctttgaacctaaatcagatagccgtgcgggttgtgggcat attgcctcgtattccggagattcacattgccattcctaatattttcagcgacgcaccgaagct tctacagagactcacgatcctcgcatactagagctgatagaaaatctacaggatgccgaggttc
```

-continued ctccattcttcattgataacggtatacttaaagcagcaccaaaaaagaaggtttctcatatgaa aagacgccagaaattatatggtccaggaaaaaaacaactctctttactacaaaatttgaacagg tgtcctgcctgcggaaactacaaacgatcacacaccctctgcatgcattgcgtaggacaaatca ggagacattggaacgactctgttcctcaacaggaggcatttcgtgaagagtttgttaatccttt ggatgagaagattctttatccaggaaagaaagaactgcccgatgaacgaactttacgtaagaag gagtggctgaagagaagaccccgaacactccctgttgaatagaacacgaacactgtaaatagaa taaaagaaaacttggatagtagaacttcaatgtagtgtttctattgtcttacgcggctctttag attgcaatccccagaatggaatcgtccatctttctcaacccactcaaagataatctaccagaca tacctacgccctccatcccagcaccacgtcgcgatcaccctaaaacttcaataattgaacacg tactgatttccaaaccttcttcttcttcctatctataaga*agatctaacatccaaagacgaaag*

*gttgaatgaaaccttttttgccatccgacatccacaggtccattctcacacataagtgccaaacg*

*caacaggagggatacactagcagcagaccgttgcaaacgcaggacctccactcctcttctcct*

*caacacccacttttgccatcgaaaaaccagcccagttattgggcttgattggagctcgctcatt*

*ccaattccttctattaggctactaacaccatgactttattagcctgtctatcctggccccctg*

*gcgaggttcatgtttgtttatttccgaatgcaacaagctccgcattacacccgaacatcactcc*

*agatgagggctttctgagtgtggggtcaaatagtttcatgttccccaaatggcccaaaactgac*

*agtttaaacgctgtcttggaacctaatatgacaaaagcgtgatctcatccaagatgaactaagt*

*ttggttcgttgaaatgctaacggccagttggtcaaaaagaaacttccaaaagtcggcataccgt*

*ttgtcttgtttggtattgattgacgaatgctcaaaaataatctcattaatgcttagcgcagtct*

*ctctatcgcttctgaaccccggtgcacctgtgccgaaacgcaaatggggaaacacccgcttttt*

*ggatgattatgcattgtctccacactgctgatagcctaacgttcatgatcaaaatttaactgtt*

*ctaaccccctacttgacagcaatatataaacagaaggaagctgccctgtcttaaaccttttttt*

*tatcatcattattagcttactttcataattgcgactggttccaattgacaagcttttgatttta*

*acgacttttaacgacaacttgagaagatcaaaaaacaactaattattgaaagaagttcctatactttct* agagaataggaacttccgaaacgatgcaattcaactggaatattaaaactgtggcaagtattttgtcc gctctcacactagcacaagcaagtgatcaggaggctattgctccagaggactctcatgtcgtca aattgactgaagccacttttgagtctttcatccagtaatcctcacgttttggcagagttttt tgccccttggtgtggtcactgtaagaagttgggccctgaacttgtttctgctgccgagatctta aaggacaatgagcaggttaagattgctcaaattgattgtacggaggagaaggaattatgtcaag gctacgaaattaaagggtatcctactttgaaggtgttccatggtgaggttgaggtcccaagtga ctatcaaggtcaaagacagagccaaagcattgtcagctatatgctaaagcagagtttacccct gtcagtgaaatcaatgcaaccaaagatttagacgacacaatcgccgaggcaaaagagcccgtga ttgtgcaagtactaccggaagatgcatccaacttggaatctaacaccacatttttacggagttgc cggtactctcagagagaaattcacttttgtctccactaagtctactgattatgccaaaaaatac actagcgactcgactcctgcctatttgcttgtcagacctggcgaggaacctagtgtttactctg gtgaggagttagatgagactcatttggtgcactggattgatattgagtccaaacctctatttgg agacattgacggatccaccttcaaatcatatgctgaagctaacatccctttagcctactatttc tatgagaacgaagaacaacgtgctgctgctgccgatattattaaaccttttgctaaagagcaac gtggcaaaattaact

Example 3

Secretory Production of Transferrin in Strain with Elevated Levels of Homologous PDI Under Methanol-Inducing Conditions in Microscale The genes encoding transferrin (SEQ ID No. 3) as well as transferrin-non-glycosylated (SEQ ID No. 4; non-glycosylated transferrin generated by double-site-directed mutagenesis to mutate both N-glycosylation motifs) were integrated into the genome of the untreated host CBS7435 muts under the control of a specifically mutated AOX1 promoter (WO 2006/089329) comprising a deletion of nucleotides 170 to 235 of SEQ ID No. 1 as identified in WO 2006/089329 and the corresponding strain with potentially elevated levels of homologous PDI as described above. Occurrence of genetic information for both transferrin variants was proven by colony PCR (forward primer binding to PAOX1, reverse primer binding to both transferrin genes within the first 80 bp). Upon cultivation in microscale, neither the basic strain CBS7435 muts host nor the strain with potentially elevated levels of homologous PDI was able to secrete transferrin in any form (to detectable levels by microfluidic capillary electrophoresis).

```
Primer sequence
(SEQ ID No. 8)
5' CAGCACACCATCTAACAG 3'

SEQ ID No. 3: Transferrin
gttccagataagactgttagatggtgtgctgtttcagagcatgaggctactaaatgtcaatctt ttagagatcacatgaagtctgtcatcccatctgatggtccatccgtggcttgtgtgaagaaagc ttcttaccttgattgtatccgggccatcgctgctaacgaagctgacgcagtccacttggacgcg ggtttagtgtacgacgcatatctagccccaaacaacttaaagccagttgtcgctgagttttacg gtagcaaggaagatccacagacattctactacgccgtcgctgttgtgaaaaaggactccggttt tcaaatgaaccagcttagagggaagaagtcatgtcataccggacttggaagatcagctggttgg aacattccaatcggtttgctgtattgcgatcttccagagccacggaagcctttggagaaggctg ttgctaatttcttttctggttcatgtgctccctgtgccgacggtaccgactttccacagttgtg ccagctgtgtccaggctgcggttgttcaacattaaaccaatacttcggttactccggtgcgttc aagtgccttaaggacggtgctggtgatgttgcgtttgttaaacattccactattttcgagaacc tggcaaataaagcagatagagatcaatacgaactgttatgcctagataacactagaaaacctgt tgacgagtacaaggactgtcaccttgcccaagtgccatctcacactgttgttgccagatcgatg ggtggtaaagaggaccttatttgggagttgctgaaccaagctcaagaacacttcggaaaggaca agtcaaaggaatttcaattgttttcttctcctcacggaaaggatttgcttttttaaggattctgc tcatggtttcttgaaggtcccaccaagaatggatgcaaaaatgtaccttggttacgagtacgta actgcgattagaaatttaagagaaggtacgtgtccagaagccccaactgatgaatgtaagccag ttaaatggtgtgcattgtctcaccacgaaagattgaagtgtgacgaatggtctgtgaactcagt tggtaaaattgagtgtgtgtcggccgaaactacggaagattgtattgcaaagatcatgaacgga gaagcagatgccatgtcactcgacggagtttcgtgtatattgccggtaagtgtggccttgttc cagttttggcagagaactacaacaaatccgataactgtgaagacactcctgaggctggctactt cgcagttgctgttgttaaaaagtctgcttcggacctaacctgggacaacctgaagggtaagaag tcttgtcacaccgcagtcgggagaaccgcaggatggaacatcccaatgggtcttctttacaata agatcaaccactgtaggtttgacgagttcttttctgaaggttgtgctcctggatctaagaagga ctcctctctttgtaaactgtgtatgggatctggtttgaacttgtgcgagccaaacaacaaggaa ggttattacggttacaccggagcttttagatgtttggttgaaaagggagacgttgccttcgtca aacaccaaactgtgcctcagaacactggtggtaagaaccccgatccttgggcaaagaatttgaa cgagaaggattacgagttattatgtttggacggtacccgtaaaccagttgaagaatacgccaat tgtcacttggctagagcaccaaaccacgccgtcgtgactagaaaagataaggaggcttgtgttc acaagatttttgcgtcaacaacaacatttgtttggatctaacgttactgattgttctggtaactt ctgtttgttccgtagcgagactaaggatctgttatttagggacgacaccgtttgcctggccaag
```

-continued
```
ttgcacgaccgtaacacttacgagaagtatttaggagaggaatacgtgaaggccgttggcaatt tgagaaagtgctctacctcttctcttttagaagcctgtacctttagaagaccttaa SEQ ID No. 4: Transferrin-non-glycosylated
gttccagataagactgttagatggtgtgctgtttcagagcatgaggctactaaatgtcaatctt ttagagatcacatgaagtctgtcatcccatctgatggtccatccgtggcttgtgtgaagaaagc ttcttaccttgattgtatccgggccatcgctgctaacgaagctgacgcagtccacttggacgcg ggtttagtgtacgacgcatatctagccccaaacaacttaaagccagttgtcgctgagttttacg gtagcaaggaagatccacagacattctactacgccgtcgctgttgtgaaaaaggactccggttt tcaaatgaaccagcttagagggaagaagtcatgtcataccggacttggaagatcagctggttgg aacattccaatcggtttgctgtattgcgatcttccagagccacggaagcctttggagaaggctg ttgctaatttcttttctggttcatgtgctccctgtgccgacggtaccgacttccacagttgtg ccagctgtgtccaggctgcggttgttcaacattaaaccaatacttcggttactccggtgcgttc aagtgccttaaggacggtgctggtgatgttgcgtttgttaaacattccactattttcgagaacc tggcaaataaagcagatagagatcaatacgaactgttatgcctagataacactagaaaacctgt tgacgagtacaaggactgtcaccttgcccaagtgccatctcacactgttgttgccagatcgatg ggtggtaaagaggaccttatttgggagttgctgaaccaagctcaagaacacttcggaaaggaca agtcaaaggaatttcaattgttttcttctcctcacggaaaggatttgcttttttaaggattctgc tcatggtttcttgaaggtcccaccaagaatggatgcaaaaatgtaccttggttacgagtacgta actgcgattagaaatttaagagaaggtacgtgtccagaagcccaactgatgaatgtaagccag ttaaatggtgtgcattgtctcaccacgaaagattgaagtgtgacgaatggtctgtgaactcagt tggtaaaattgagtgtgtgtcggccgaaactacggaagattgtattgcaaagatcatgaacgga gaagcagatgccatgtcactcgacggaggtttcgtgtatattgccggtaagtgtggccttgttc cagttttggcagagaactaccaaaaatccgataactgtgaagacactcctgaggctggctactt cgcagttgctgttgttaaaaagtctgcttcggacctaacctgggacaacctgaagggtaagaag tcttgtcacaccgcagtcgggagaaccgcaggatggaacatcccaatgggtcttctttacaata agatcaaccactgtaggtttgacgagttcttttctgaaggttgtgctcctggatctaagaagga ctcctctctttgtaaactgtgtatgggatctggtttgaacttgtgcgagccaaacaacaaggaa ggttattacggttacaccggagcttttagatgtttggttgaaaagggagacgttgccttcgtca aacaccaaactgtgcctcagaacactggtggtaagaaccccgatccttgggcaaagaatttgaa cgagaaggattacgagttattatgtttggacggtacccgtaaaccagttgaagaatacgccaat tgtcacttggctagagcaccaaaccacgccgtcgtgactagaaaagataaggaggcttgtgttc acaagattttgcgtcaacaacaacatttgtttggatctcaagttactgattgttctggtaactt ctgtttgttccgtagcgagactaaggatctgttatttagggacgacaccgtttgcctggccaag ttgcacgaccgtaacacttacgagaagtatttaggagaggaatacgtgaaggccgttggcaatt tgagaaagtgctctacctcttctcttttagaagcctgtacctttagaagaccttaa
```

Example 4

Figure 3:
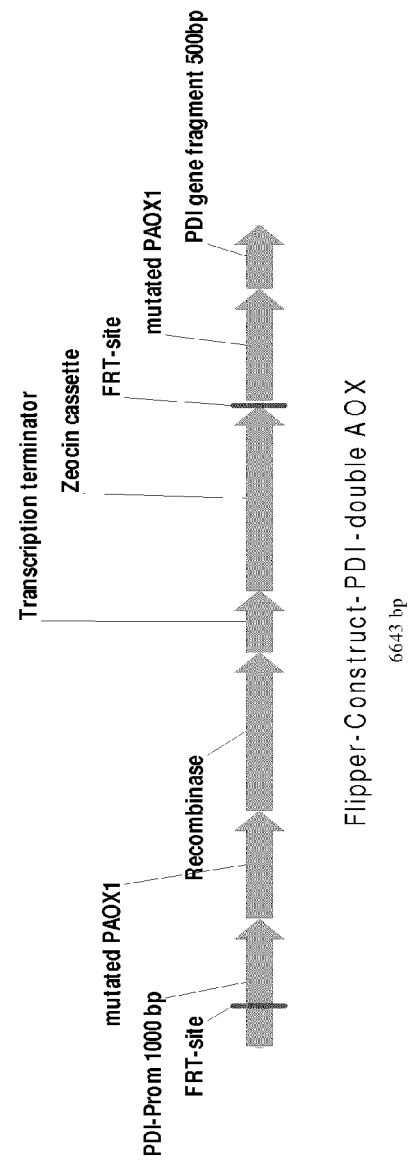
FIG. 3 shows a plasmid map of "Flipper construct" for promoter replacement cassette of native Protein Disulfide Isomerase (PDI) promoter by a specifically mutated AOX1 promoter.

Construction of Promoter Replacement Cassette of Native Protein Disulfide Isomerase (PDI) Promoter by Specifically Mutated AOX1 Promoter The transformed DNA construct consists of the first 1000 bp of the homologous PDI promoter (based on the assumption that the native PDI promoter may consist of approximately 1000 bp), and a specifically regulated, mutated AOX1 promoter (WO 2006/089329) driving the expression of Flp recombinase, followed by CYC1 transcription terminator and a Zeocin resistance cassette (functional in E. coli by EM72 promoter, and in P. pastoris by ILV5 promoter and AOD transcription terminator), further followed by a differently regulated, specifically mutated AOX1 promoter (WO 2006/089329) and the first 500 bp of the homologous PDI gene. The recombinase recognition sites are placed after the first 300 bp of the homologous promoter, and directly upstream of the second specific AOX1 promoter (FIG. 3). This DNA fragment was ordered as synthetically generated DNA with DNA2.0 (Menlo Park, USA).

Example 5

Transformation of Construct into CBS7435 Mots, Confirmation of Genomic Constellation, Propagation on Methanol Media and Cassette Excision and Confirmation After transformation and selection on agar-plates, 20 colonies were confirmed by colony PCR to carry the integrated transformation cassette in the correct genomic orientation.

Figure 4:
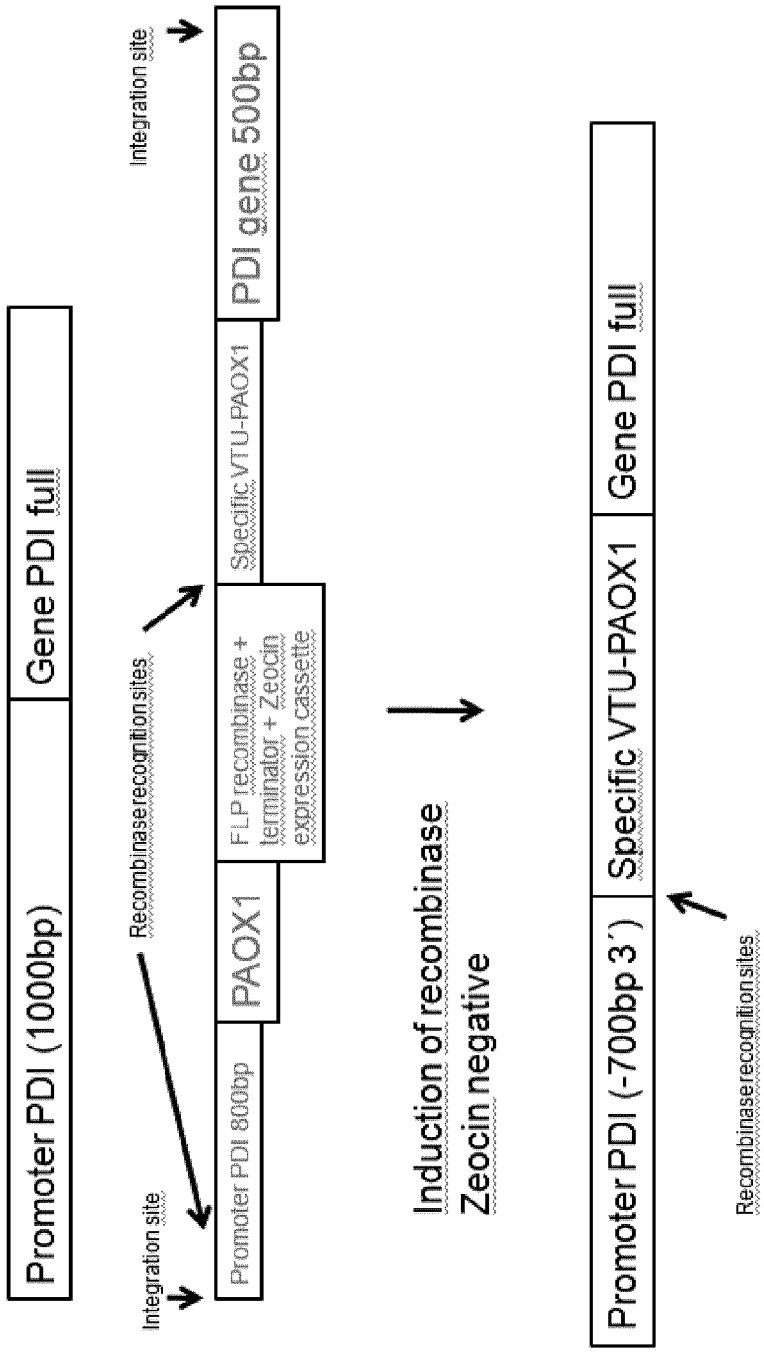
FIG. 4 shows a graphic chart of promoter replacement strategy for PDI promoter.

Clones were transferred to minimal methanol agar plates for 5 days (until large single colonies are formed), in total 3 consecutive times. Thereafter, excision of the DNA region between the FRT sites (most part of the homologous promoter region, strong inducible AOX1 promoter and Flp recombinase, resistance marker cassette) was checked by counter-restreaking on YPhyD plates containing selection marker (Zeocin): positive clones, i.e. those where excision took place, were not able to grow on these plates. Colony PCR proved the occurrence of upstream part of homologous promoter only, and adjacent specific AOX1 promoter and homologous PDI gene (FIG. 4, SEQ ID No. 5).

SEQ ID No. 5: sequence obtained for genomic PDI locus
Bold: truncated native PDI promoter region (starting with base at former position 1000 bp upstream of native PDI gene), 333 bp left
Italic: mutated AOX1 promoter
Regular: native PDI gene (first 892 bases) with 5' kozak sequence
Subscript: FRT site aagggagacatattcggctattgtttactttgcgcccacagtagcgttaagaaacattgtttgt tcgatttattgggctgttgataaattcaattgattacgttcgcatactagctatcataaactaa gcaccaccttacaccactttctcactgaagattttcgacatcaaatttctcttggatcaccatc aaccttgtgtctacatgtccttgtctttgaacctaaatcagatagccgtgcgggttgtgggcat attgcctcgtattccggagattcacattgccattcctaatattttcagcgacgcaccgaagct tctacagagactc$_{gaagttcctatactttctagagaataggaacttc}$agatctaacatccaaagacgaaagg ttgaatgaaaccttttttgccatccgacatccacaggtccattctcacacataagtgccaaacgc aacaggaggggatacactagcagcagaccgttgcaaacgcaggacctccactcctcttctcctc aacacccacttttgccatcgaaaaaccagcccagttattgggcttgattggagctcgctcattc caattccttctattaggctactaacaccatgactttattagcctgtctatcctggccccctgg cgaggttcatgtttgtttatttccgaatgcaacaagctccgcattacacccgaacatcactcca gatgagggctttctgagtgtggggtcaaatagtttcatgttccccaaatggcccaaaactgaca gtttaaacgctgtcttggaacctaatatgacaaaagcgtgatctcatccaagatgaactaagtt tggttcgttgaaatgctaacggccagttggtcaaaaagaaacttccaaaagtcggcataccgtt tgtcttgtttggtattgattgacgaatgctcaaaaataatctcattaatgcttagcgcagtctc tctatcgcttctgaacccggtgcacctgtgccgaaacgcaaatggggaaacaccgcttttg gatgattatgcattgtctccacactgctgatagcctaacgttcatgatcaaaatttaactgttc taaccctacttgacagcaatatataaacagaaggaagctgccctgtcttaaaccttttttttt atcatcattattagcttactttcataattgcgactggttccaattgacaagcttttgattttaa cgactttaacgacaacttgagaagatcaaaaaacaactaattattgaattccgaaacgatgca attcaactggaatattaaaactgtggcaagtattttgtccgctctcacactagcacaagcaagt gatcaggaggctattgctccagaggactctcatgtcgtcaaattgactgaagccacttttgagt ctttcatcaccagtaatcctcacgttttggcagagttttttgcccttggtgtggtcactgtaa gaagttgggccctgaacttgtttctgctgccgagattttaaaggacaatgagcaggttaagatt gctcaaattgattgtacggaggagaaggaattatgtcaaggctacgaaattaaagggtatccta ctttgaaggtgttccatggtgaggttgaggtcccaagtgactatcaaggtcaaagacagagcca aagcattgtcagctatatgctaaagcagagtttaccccctgtcagtgaaatcaatgcaaccaaa gatttagacgacacaatcgccgaggcaaaagagcccgtgattgtgcaagtactacctgcagcgg aagatgcatccaacttggaatctaacaccacattttacggagttgccggtactctcagagagaa attcacttttgtctccactaagtctactgattatgccaaaaaatacactagcgactcgactcct

```
gcctatttgcttgtcagacctggcgaggaacctagtgtttactctggtgaggagttagatgaga ctcatttggtgcactggattgatattgagtccaaacctctatttggagacattgacggatccac cttcaaatcatatgctgaagctaacatccctttagcctactatttctatgagaacgaagaacaa cgtgctgctgctgccgatattattaaaccttttgctaaagagcaacgtggcaaaattaactt
```

By excision of the resistance cassette, a counter-selection on this antibiotic revealed positive strains by a negative growth behaviour (i.e. no resistance to anbitiotic). Additionally colony PCR confirmed the intended genomic constellation. One of the positive strains was selected and named CBS7435 muts PDI platform.

Example 6

Secretory Production of Transferrin in Strain with Elevated Levels of Homologous PDI Under Methanol-Inducing Conditions in Microscale The genes encoding transferrin as well as transferrin-non-glycosylated (see Example 3) were integrated into the genome of the untreated host CBS7435 muts under the control of a specifically mutated AOX1 promoter (WO 2006/089329) and the corresponding strain with potentially elevated levels of homologous PDI as described above. Occurrence of genetic information for both transferrins was proven by colony PCR (forward primer binding to PAOX1, reverse primer binding to both transferrin genes within the first 80 bp). Upon cultivation in microscale, the basic strain CBS7435 muts host was not able to secrete transferrin in any form (to detectable levels by microfluidic capillary electrophoresis), while the strain with potentially elevated levels of homologous PDI produced both transferrin variants detectable in the supernatant (Table 1, FIGS. 5 and 6). This was indicative of augmenting PDI activity by the specifically mutated PAOX1 high enough to promote folding/secretion of both transferrin variants, as opposed to the basic strain.

TABLE 1

Titers of target protein in microscale culture supernatants for transferrin and transferrin-non-glycosylated produced by strains CBS7435 muts, and CBS7435 muts PDI platform, respectively.

| Strain | Transferrin mg/L | Transferrin-non-glycosylated mg/L |
| --- | --- | --- |
| CBS7435 muts | 0 | 0 |
| CBS7435 muts PDI platform | 20 | 40 |

Example 7

Secretory Production of Transferrin and Transferrin-Non-Glycosylated in Strain with Elevated Levels of Homologous PDI Under Methanol-Inducing Conditions in Bioreactor Cultivations CBS7435 muts PDI platform strains with integrated transferrin and transferrin-non-glycosylated expression cassettes and proven secretion rates (as compared to the non-secreting CBS7435 muts strains) were cultivated under controlled conditions in 1 L bioreactors. After a total process time of 109 hours (90 hours of methanol induction), the fermentation supernatant was assayed by microfluidic capillary electrophoresis. After a dilution series and comparison to internal and external standards, high concentrations of both proteins were detectable (Table 2).

TABLE 2

Estimated titers of target protein in bioreactor culture supernatants for transferrin and transferrin-non-glycosylated produced by strain CBS7435 muts PDI platform.

| Strain | Transferrin g/L | Transferrin-non-glycosylated g/L |
| --- | --- | --- |
| CBS7435 muts PDI platform | 5.4 | 5.2 |

Example 8

Measurement of Transcript Levels of Homologous PDI in Basic Strain CBS7435 Muts and Strain with Potentially Elevated Levels of Homologous PDI Transcript levels (based on specific primers hybridized to present mRNA) were analyzed from fermentation samples in batch phase (glycerol present in large amounts), glycerol fed-batch phase (glycerol present in derepressive amounts) and several time-points during the methanol induction phase (production phase for recombinant protein(s)) (PlexPress, Helsinki, Finland). Equal biomass amounts of CBS7435 muts and CBS7435 muts PDI platform without integrated recombinant expression cassette. Normalization was further done by comparison to expression levels of housekeeping genes in order to relate to metabolically active cells.

While during batch phase (high glycerol), mRNA levels of native PDI1 gene was elevated in CBS7435 muts strain (due to repressive effects of glycerol on the specific AOX1 promoter regulating the expression of PDI1 gene in CBS7435 muts PDI platform strains), upon derepressive conditions (glycerol fed-batch) and during all steps of methanol induction (production phase for recombinant protein(s)) mRNA levels of native PDI1 gene were increased by 60-fold in CBS7435 muts PDI platform strain as opposed to CBS7435 muts.

Example 9

Secretory Production of Interleukin-2 and Human Serum Albumin (HSA) in Strain with Elevated Levels of Homologous PDI Under Methanol-Inducing Conditions in Microscale and Under Bioreactor Conditions In analogy to above described examples for transferrin and transferrin-non-glycosylated, the expression cassette for interleukin-2 (SEQ ID No. 6) or HSA (SEQ ID No. 7) was transformed into the genome of the untreated host CBS7435 muts under the control of a specifically mutated AOX1 promoter (WO 2006/089329) and the corresponding strain with elevated levels of homologous PDI as described above. Occurrence of genetic information for both genes was proven by colony PCR (forward primer binding to PAOX1, reverse primer binding to interleukin-2 or HSA gene within the first 80 bp).

Upon cultivation in microscale, both strains (basic strain CBS7435 muts as well as the strain with elevated levels of homologous PDI) secreted interleukin-2 or HSA, but under bioreactor conditions almost 2-fold higher yields for HSA and 4-fold higher yields for interleukin-2 were achieved by CBS7435 muts PDI platform strain.

```
Primer HSA
                                                          (SEQ ID No. 9)
5' GGTCCTTGAATCTATGAG 3'

Primer IL2
                                                          (SEQ ID No. 10)
5' CGTAGAAGAAGAGGTTGG 3'

IL-2
                                                          SEQ ID No. 6
gcaccaacctcttcttctacgaaaaagactcagcttcaattggagcacctttactggacttgc aaatgatcctgaacggtatcaacaactacaaaaaccctaaacttactagaatgttgaccttcaa gttttacatgccaaagaaggctaccgaattgaagcacttgcaatgtctggaggaggagttgaag ccattggaagaagtttttgaacttggcacagtcgaagaacttccaccttagacctagagacttga tttctaacatcaacgtcatcgtcctggagcttaaggggtccgagactactttcatgtgtgagta cgctgacgagacagcgactattgtcgagttcttgaatagatggatcactttcgcccaatccatt atctccaccttaacctaa HSA
                                                          SEQ ID No. 7
gatgcacacaaatcagaagttgctcatagattcaaggacctcggagaagagaacttcaaggctc ttgtccttatcgctttcgctcaataccttcagcaatgtccttttgaggaccacgttaagttggt gaacgaagttaccgagttcgctaaaacttgcgtagctgacgaatctgctgagaactgtgacaag tcacttcacactctttttggtgacaagctttgtactgtcgctaccccttcgtgaaacctacggcg aaatggccgattgctgtgctaagcaggaacctgaaagaaacgaatgtttcttgcagcacaagga cgataaccccaatcttcctcgtttggttcgtcctgaggtcgacgttatgtgcaccgcttttcat gacaacgaagagactttcttaaagaaatacctttacgaaatcgctcgtcgtcacccatacttct acgctccagagctgttgttcttcgcaaagagatataaggctgctttcactgagtgttgccaagc tgctgacaaggcagcttgtctattgcctaagcttgacgaattgcgagatgagggtaaagcatct tccgccaagcagagattgaaatgcgcttccttgcagaagtttggtgagcgagctttcaaagcct gggccgtggctaggttgagccaacgttttcctaaagctgagttcgctgaagtttctaagttggt tactgatcttactaaggtgcacactgaatgttgccacggtgaccttctggagtgtgctgatgac cgtgcagatttggctaagtatatttgtgaaaaccaagattctatttcttctaaactaaaggaat gttgtgaaaagccacttcttgagaaaagtcactgtatcgctgaggtggagaacgacgagatgcc agctgaccttcctagcctggctgctgatttcgttgaatctaaggacgtatgcaagaattacgca gaggccaaggatgttttccttggcatgttttttgtacgagtacgctagaagacaccctgactact ccgtagttctcttgctgaggttggcaaagacctacgagactaccctagagaagtgttgcgccgc agctgatcctcacgagtgttatgctaaagtttttgatgagtttaaacctttggttgaggagcca caaaacttgattaagcagaactgcgagcttttcgaacaattgggggaatacaagttccaaaatg ccttgctagtcaggtacaccaaaaaggtccctcaggtcagcaccccaaccttagtcgaggtgtc cagaaatttgggcaaagttggttctaaatgttgcaagcacccagaagctaagaggatgccatgt gccgaagactacctttccgtcgttctgaaccaactctgtgttttgcacgaaaagactccagtct cagaccgtgtcacgaaatgttgtaccgagtctctggttaacagaagaccttgtttctctgctttt
```

```
ggaagttgacgaaacttacgtcccaaaggagttcaacgcggagactttcaccttccacgccgac atttgtacactttccgagaaggaaagacaaatcaagaagcaaaccgcactagttgaattggtta aacataagcctaaggctaccaaagaacaattgaaagcagttatggatgattttgcggctttcgt ggaaaagtgttgtaaggctgatgacaaggaaacctgtttcgccgaagaaggtaagaagttagtc gccgcctctcaggctgctcttggactgtaa
```

Summary:

A correct double crossover of the recombination cassette in the PDI promoter (5' homology) and the beginning of the PDI gene (3' homology) led to an insertional integration of the recombinase expression cassette, the resistance cassette and the specific AOX1 promoter variant between the native PDI promoter and the native PDI gene. Continuous growth on glycerol or glucose strongly repressed the transcription from the AOX1 promoter variant driving the expression of the recombinase, and hence no excision took place under such conditions.

Upon growth on methanol-containing media, transcription of the recombinase gene started and subsequently resulted in excision of the DNA fragment between the two Flp recombinase recognition sites, thereby excising large parts of the native PDI promoter, the recombinase expression cassette as well as the resistance cassette, leaving behind only the specifically mutated AOX1 promoter directly upstream of the native PDI gene.

In an alternative approach with a direct integration of the specifically mutated PAOX1 between the native PDI promoter and the PDI gene, expression of transferrin and transferrin-non-glycosylated was not possible. This might be due to repression effects triggered by the native PDI promoter upstream, or inefficient transcription of the PDI gene from the mutated PAOX1 caused by the remaining FRT site between the mutated AOX1 promoter and the PDI gene.

By excision of the resistance cassette, a counter-selection on this antibiotic revealed positive strains by a negative growth behavior (i.e. no resistance to antibiotic). Additionally colony PCR confirmed the intended genomic constellation. One of the positive strains was selected and named CBS7435 muts PDI platform.

Cultivation of the parental strain CBS7435 muts and the newly generated CBS7435 muts PDI platform were cultivated under controlled, classical methanol-inducing conditions in 1 L bioreactors, without the heterologous expression of any target gene from a recombinant expression cassette. Transcript levels for the native PDI for both strains at different time-points of the cultivation revealed that under glycerol batch conditions, occurrence of mRNA for PDI1 gene was higher in the parental strain as compared to CBS7435 muts PDI platform. Upon supply with low levels of glycerol as well as under methanol-inducing conditions, significantly more mRNA (60-fold) was present in CBS7435 muts PDI platform strain as compared to CBS7435 muts.

Figure 5:
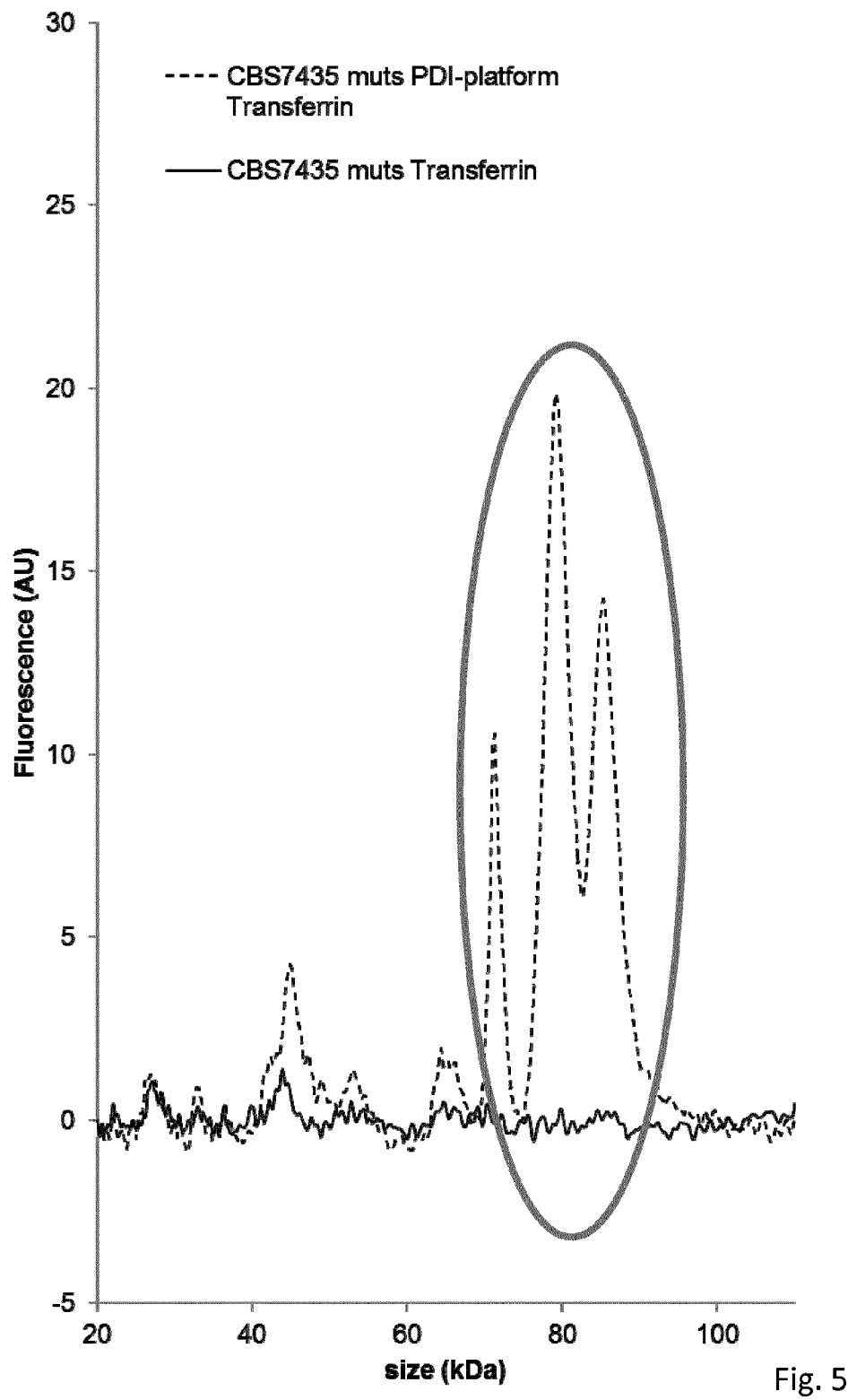
FIG. 5 shows an electropherogram overlay (GXII, Caliper Life Sciences, USA) of (directly applied) supernatant of transferrinexpressing strain CBS7435 muts (full line), and CBS7435 muts PDI platform (dashed line), respectively.
Figure 6:
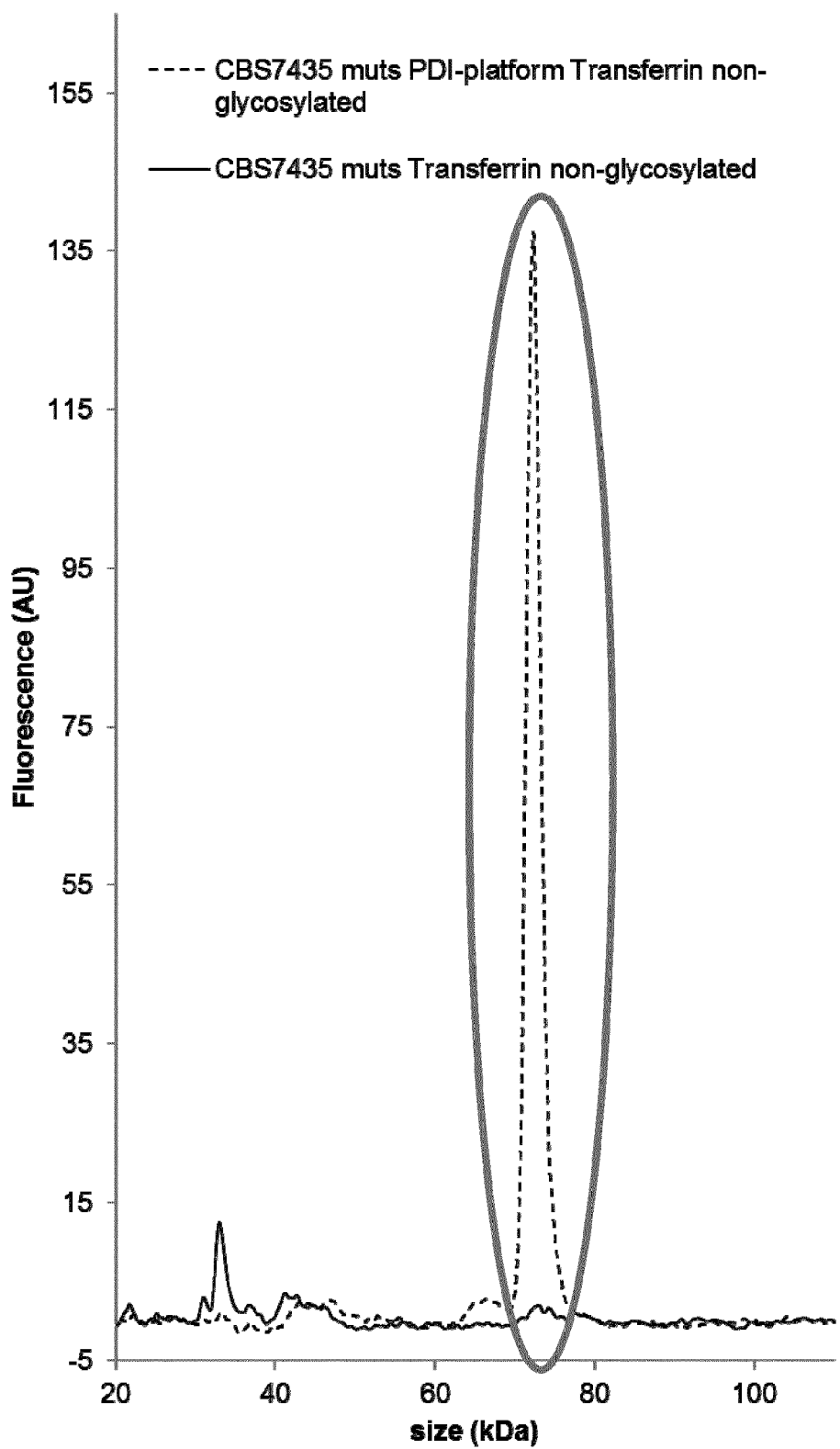
FIG. 6 shows an electropherogram overlay (GXII, Caliper Life Sciences, USA) of (directly applied) supernatant of transferrinnon-glycosylated-expressing strain CBS7435 muts (full line) and CBS7435 muts PDI platform (dashed line), respectively.

In order to verify the required amount of increased levels of native PDI for secretory expression of transferrin and/or transferrin-non-glycosylated, both genes were (separately) transformed into both strains, CBS7435 muts and CBS7435 muts PDI platform. After microscale cultivation, supernatants were analyzed by microfluidic capillary electrophoresis. While in CBS7435 muts no target protein was detectable, CBS7435 muts PDI platform obviously produced enough native PDI (by transcriptional over-regulation of the introduced AOX1 promoter variant) to efficiently secrete both proteins (FIGS. 5 and 6). Bioreactor cultivation under controlled methanol-inducing conditions confirmed the presence of both highly disulfide-bonded target proteins in high concentrations.

Application of specific AOX1 promoter variants (WO 2006/089329) for increased production of transferrin and transferrin-non-glycosylated under methanol-free conditions also proved to work efficiently in microscale and bioreactor conditions, using CBS7435 muts PDI platform strain for expression.

For target proteins that are also produced in high levels by CBS7435 muts strain, i.e. without an increase of native PDI or overproduction of heterologous PDI, as e.g. Human Serum Albumin (HSA), CBS7435 muts PDI platform strain provides a means of augmenting production levels as well. While with CBS7435 muts 8 g/L of HSA were produced in the culture supernatant, CBS7435 muts PDI platform secreted 14 g/L of HSA under identical conditions concerning promoter usage, integrated copy number of expression cassette and culture conditions.

As HSA requires the formation of 17 disulfide bonds, a further model protein was tested which needs only 1 disulfide bond to be formed for its native fold. Interleukin-2 was expressed to 4-fold higher yield from CBS7435 muts PDI platform strain as compared to CBS7435 muts strain under controlled conditions in a bioreactor.

Example 10

Secretory Production of an HSA-Fusion Protein (HSA-Interferon(Alpha2a)) in Strain with Elevated Levels of Homologous PDI Under Methanol-Inducing Conditions in Microscale in Direct Comparison to Secretory Production in Strain with Recombinantly Expressed "Native" PDI in One Copy, and Wildtype Strain with no Modification In analogy to above described examples, the expression cassette for HSA-Interferon(alpha2a) (SEQ ID No. 16) under the control of a specifically mutated AOX1 promoter (WO 2006/089329) was transformed into the genome of the untreated host CBS7435 muts and the corresponding strain with elevated levels of homologous PDI as described above. Additionally, the untreated host strain CBS7435 muts was transformed with both, the expression cassette for HSA-Interferon(alpha2a) and a different plasmid harboring an expression cassette of the native PDI gene under the control of the same mutated AOX1 promoter that is controlling expression of the native PDI gene in the strain with elevated levels of homologous PDI. Occurrence of genetic information for all introduced genes was proven by colony PCR (forward primer binding to PAOX1, reverse primer binding to interferon (alpha2a) or HSA gene within the first 80 bp). Occurrence of genetic information for the recombinantly introduced native PDI gene was proven by colony PCR (forward primer binding to native PDI gene, reverse primer binding to resistance marker against Geneticin).

Upon cultivation in microscale, all 3 strains (basic strain CBS7435 muts, strain with elevated levels of homologous PDI, and basic strain co-expressing the native PDI also recombinantly) secreted HSA-Interferon(alpha2a). While co-expressing the native PDI gene recombinantly increased secreted levels of HSAInterferon(alpha2a) by ~60% as compared to basic strain CBS7435 muts, the strain with elevated levels of homologous PDI further augmented titers by 57% when compared to basic strain co-expressing the native PDI also recombinantly (FIG. 7)

```
Primer Interferon(alpha2a)
                                                        (SEQ ID No. 13)
5' CTTGAACCCAATGAGTGTG 3'

Primer native PDI
                                                        (SEQ ID No. 14)
5' GAAGCTGAAGAAGAAGCTG 3'

Primer resistance marker
                                                        (SEQ ID No. 15)
5' GATTGTCGCACCTGATTGCC 3'

HSA-Interferon(alpha2a)
regular: HSA
underlined: interferon(alpha2a)
                                                        SEQ ID No. 16
gatgcacacaaatcagaagttgctcatagattcaaggacctcggagaagagaacttcaaggctc ttgtccttatcgctttcgctcaataccttcagcaatgtccttttgaggaccacgttaagttggt gaacgaagttaccgagttcgctaaaacttgcgtagctgacgaatctgctgagaactgtgacaag tcacttcacactcttttggtgacaagctttgtactgtcgctacccttcgtgaaacctacggcg aaatggccgattgctgtgctaagcaggaacctgaaagaaacgaatgtttcttgcagcacaagga cgataaccccaatcttcctcgtttggttcgtcctgaggtcgacgttatgtgcaccgcttttcat gacaacgaagagactttcttaaagaaatacctttacgaaatcgctcgtcgtcacccatacttct acgctccagagctgttgttcttcgcaaagagatataaggctgctttcactgagtgttgccaagc tgctgacaaggcagcttgtctattgcctaagcttgacgaattgcgagatgagggtaaagcatct tccgccaagcagagattgaaatgcgcttccttgcagaagtttggtgagcgagctttcaaagcct gggccgtggctaggttgagccaacgttttcctaaagctgagttcgctgaagtttctaagttggt tactgatcttactaaggtgcacactgaatgttgccacggtgaccttctggagtgtgctgatgac cgtgcagatttggctaagtatatttgtgaaaaccaagattctatttcttctaaactaaaggaat gttgtgaaaagccacttcttgagaaaagtcactgtatcgctgaggtggagaacgacgagatgcc agctgaccttcctagcctggctgctgatttcgttgaatctaaggacgtatgcaagaattacgca gaggccaaggatgttttccttggcatgtttttgtacgagtacgctagaagacaccctgactact ccgtagttctcttgctgaggttggcaaagacctacgagactaccctagagaagtgttgcgccgc agctgatcctcacgagtgttatgctaaagttttttgatgagtttaaacctttggttgaggagcca caaaacttgattaagcagaactgcgagcttttcgaacaattgggggaatacaagttccaaaatg ccttgctagtcaggtacaccaaaaaggtccctcaggtcagcaccccaaccttagtcgaggtgtc cagaaatttgggcaaagttggttctaaatgttgcaagcacccagaagctaagaggatgccatgt gccgaagactacctttccgtcgttctgaaccaactctgtgttttgcacgaaaagactccagtct cagaccgtgtcacgaaatgttgtaccgagtctctggttaacagaagaccttgtttctctgcttt ggaagttgacgaaacttacgtcccaaaggagttcaacgcggagactttcaccttccacgccgac atttgtacactttccgagaaggaaagacaaatcaagaagcaaaccgcactagttgaattggtta aacataagcctaaggctaccaaagaacaattgaaagcagttatggatgattttgcggctttcgt ggaaaagtgttgtaaggctgatgacaaggaaacctgtttcgccgaagaaggtaagaagttagtc gccgcctctcaggctgctcttggact```gtgcgacttgcctcaaacacactcattgggttcaagac```

```gtactttaatgcttctcgctcagatgagaaagatttctctgttctcttgtctaaaggaccgtca```

```
                                                            -continued
cgacttcggttttccacaagaggaatttggaaaccaattccaaaaagctgagactattcccgtt ttacacgaaatgatccaacagattttcaacctttctctactaaggattcttccgctgcatggg acgaaactttgctcgacaaattctacaccgaactttaccaacagcttaatgacctagaagcctg cgtgatacaggggcgtcggtgtcacagaaacgccattgatgaaggaggatagcatcttggccgtg cgtaagtatttccaaagaattactttgtaccttaaggaaaagaaatactctccttgtgcttggg aagtagtcagagctgaaattatgagatcctttccctttctactaacttgcaagagtccttaag atcgaaggaataa
```

Example 11

Secretory Production of a Fab (Fragment AntigenBinding) Molecule in Strain with Elevated Levels of Homologous Kar2 Under Methanol-Inducing Conditions in Microscale in Direct Comparison to Secretory Production in Strain with Recombinantly Expressed "Native" Kar in One Copy, and Wildtype Strain with No Modification In analogy to above described examples, the expression cassettes for the light chain of Fab (SEQ ID No. 20) and the heavy chain of Fab (SEQ ID No. 21) under the control of a specifically mutated AOX1 promoter (WO 2006/089329) were transformed into the genome of the untreated host CBS7435 muts and the corresponding strain with elevated levels of homologous Kar2. Additionally, the untreated host strain CBS7435 muts was transformed with the expression cassettes for light and heavy chain and a different plasmid harboring an expression cassette of the native Kar2 gene under the control of the same mutated AOX1 promoter that is controlling expression of the native Kar2 gene in the strain with elevated levels of homologous Kar2. Occurrence of genetic information for all introduced genes was proven by colony PCR (forward primer binding to PAOX1, reverse primer binding to the light and heavy chain genes within the first 80 bp). Occurrence of genetic information for the recombinantly introduced native Kar2 gene was proven by colony PCR (forward primer binding to native PDI gene, reverse primer binding to resistance marker against Geneticin).

Upon cultivation in microscale, all 3 strains (basic strain CBS7435 muts, strain with elevated levels of homologous Kar2, and basic strain co-expressing the native Kar2 also recombinantly) secreted Fab. While co-expressing the native Kar2 gene recombinantly increased secreted levels of Fab by ~47% as compared to basic strain CBS7435 muts, the strain with elevated levels of homologous Kar2 further augmented titers by 27% when compared to basic strain co-expressing the native Kar2 also recombinantly (FIG. 8)

```
Primer Fab light chain
                                                            (SEQ ID No. 17)
5' CAGAAACGGAAGGAGGTTG 3'

Primer Fab heavy chain
                                                            (SEQ ID No. 18)
5' CTGACTTCAGCTCCAGATTG 3'

Primer Kar2
                                                            (SEQ ID No. 19)
5' GTACTCCACCTGGTGGTC 3'

Fab light chain
                                                              SEQ ID No. 20
caatccgtcctgacccaacctccttccgtttctgctgctcctggtcaaaaggtcaccatttcct gttctggatcttcatctaacattggaaagaattacgtttcctggtaccaacagttaccaggtgc tgcacctaagttacttatctttgatgacactcaaagaccatccggaatcccagacagattctct ggttctaagtctggtacttccgcaaccctggccatcaccggattgcagactggtgatgaggccg actactattgcggtacttgggactcttctctgtctactggtcaacttttcggaggtggtaccaa attgaccgttttgggtcagcctaaggctgctccatctgttactcttttcctccatcttcagag gaattgcaggccaacaaggctactcttgtttgtttgatttctgacttctaccctggtgcagtca ctgtggcatggaaagctgattcatctccagtcaaagctggtgtggagactaccactccatctaa gcaatctaacaacaaatacgcagcttcatcctatttgtctttgacccagagcagtggaagtcc caccgttcatactcctgtcaagttacccatgagggttctactgttgaaaagactatggcccacg ctgaatgctcctaa
```

Fab heavy chain

SEQ ID No. 21 caagtgcaagttgttcaatctggagctgaagtcagaaagccaggagcttctgttaaagtgtcat gtaaagtttctggtttcactttgaccggtttatccattcactgggttagacaagcacctggtaa aggtttggaatggatgggtggatttggtccagaggaaaatgagattatctatgctcaaaagttc cagggtagagtctccatgaccgaggacacttccaccaatactgcatacatggaattgtcctctc ttagatcagaagatactgctgtctactattgtgctactggtggtaactattacaacttgtggac tggttactacccttagcttactggggtcagggtactctggttactgtctcttcagcctctact aagggaccatctgttttccacttgctccttcctctaagtccacctctggtggaaccgctgcac tgggttgtttggtcaaggattacttcccagagccagttaccgtgtcttggaactctggtgccct tacttctggtgtccataccttcccagccgttttgcagtcatctggactttactccctttcctct gttgtcactgttccttcctcctctttgggaactcaaacctacatctgcaacgttaaccacaagc cttctaacaccaaggttgacaaaaaggtggagcctaagtcttgctaa

---

The invention claimed is:

1. A method for producing a recombinant protein or polypeptide of interest comprising the steps of:
provding a genetically modified yeast cell comprising
a) an expression secretion cassette comprising a recombinant nucleic acid molecule encoding a protein or polypeptide of interest and
b) at least one recombinant promoter operably linked to at least one gene naturally occurring in the genome of the yeast cell and encoding a polypeptide or protein supporting the biosynthesis of polypeptides or proteins within said cell, said at least one gene being located at the native genomic locus of the genetically unmodified wild-type yeast cell, wherein the naturally occurring promoter of the at least one gene encoding the biosynthesis supporting polypeptide or protein is inactivated by at least one mutation within said naturally occurring promoter,
cultivating said genetically modified yeast cell in a culture medium under conditions that allow for expression of the protein or polypeptide of interest and the at least one gene encoding the biosynthesis supporting polypeptide or protein and
isolating the protein or polypeptide of interest from the culture medium.

2. The method according to claim 1, characterized in that said at least one recombinant promoter enables the genetically modified yeast cell to produce at least 100% more of the polypeptide or protein supporting the biosynthesis of polypeptides or proteins compared to the genetically unmodified wild-type yeast cell.

3. The method according to claim 1, characterized in that the at least one gene encoding a polypeptide or protein supporting the biosynthesis of polypeptides or proteins within said cell is a chaperone.

4. The method according to claim 3, characterized in that the chaperone is selected from the group consisting of protein disulfide isomerase, binding protein Kar2/BiP and calnexin.

5. The method according to claim 1, characterized in that the recombinant promoter is an inducible genetically modified or unmodified yeast promoter.

6. The method according to claim 5, characterized in that the yeast promoter is selected from the group consisting of AOX1 promoter, GAL1 promoter, PGK promoter, ADH promoter, FDH promoter and FLD promoter.

7. The method according to claim 1, characterized in that the yeast cell is a methylotrophic yeast cell.

8. The method according to claim 1, characterized in that the at least one mutation of the naturally occurring promoter of the at least one gene encoding the biosynthesis supporting polypeptide or protein is a deletion.

9. The method according to claim 8, characterized in that at least 50 nucleotides of the naturally occurring promoter of the at least one gene encoding the biosynthesis supporting polypeptide or protein is deleted.

10. A genetically modified yeast cell comprising at least one recombinant promoter operably linked to at least one gene naturally occurring in the genome of the yeast cell and encoding a polypeptide or protein supporting the biosynthesis of polypeptides or proteins within said cell, said at least one gene being located at the native genomic locus of the genetically unmodified wild-type yeast cell, wherein the naturally occurring promoter of the at least one gene encoding the biosynthesis supporting polypeptide or protein is inactivated by at least one mutation within said naturally occurring promoter and an expression secretion cassette comprising a recombinant nucleic acid molecule encoding a protein or polypeptide of interest.

11. The cell according to claim 10, characterized in that said at least one recombinant promoter enables the genetically modified yeast cell to produce at least 100% more of the polypeptide or protein supporting the biosynthesis of polypeptides or proteins compared to the genetically unmodified wild-type yeast cell.

12. The cell according to claim 10, characterized in that the at least one gene encoding a polypeptide or protein supporting the biosynthesis of polypeptides or proteins within said cell is a chaperone.

13. The cell according to claim 12, characterized in that the chaperone is selected from the group consisting of protein disulfide isomerase, binding protein Kar2/BiP and calnexin.

14. The cell according to claim 10, characterized in that the recombinant promoter is an inducible genetically modified or unmodified yeast promoter.

15. The cell according to claim 14, characterized in that the yeast promoter is selected from the group consisting of AOX1 promoter, GAL1 promoter, PGK promoter, ADH promoter, FDH promoter and FLD promoter.

16. The cell according to claim 15, characterized in that the yeast promoter is an AOX1 promoter comprising at least one mutation within nucleotides 170 to 235 or 694 to 723 or 694 to 723 and 737 to 738 of SEQ ID No. 1.

17. The cell according to claim 10, characterized in that the yeast cell is a methylotrophic yeast cell.

18. The cell according to claim 10, characterized in that the at least one mutation of the naturally occurring promoter of the at least one gene encoding the biosynthesis supporting polypeptide or protein is a deletion.

19. The cell according to claim 18, characterized in that at least 50 nucleotides of the naturally occurring promoter of the at least one gene encoding the biosynthesis supporting polypeptide or protein is deleted.

20. The cell according to claim 10, characterized in that the nucleic acid molecule encoding a protein or polypeptide of interest is part of a vector or integrated into the genome.

21. The method of claim 1, characterized in that said at least one recombinant promoter enables the genetically modified yeast cell to produce at least 200% more of the polypeptide or protein supporting the biosynthesis of polypeptides or proteins compared to the genetically unmodified wild-type yeast cell.

22. The cell according to claim 10, characterized in that said at least one recombinant promoter enables the genetically modified yeast cell to produce at least 200% more of the polypeptide or protein supporting the biosynthesis of polypeptides or proteins compared to the genetically unmodified wild-type yeast cell.

23. The method according to claim 1, characterized in that the yeast cell is a methylotrophic yeast cell selected from the group consisting of a yeast of the genus of *Pichia, Candida boidinii* and *Hansenula polymorpha*.

24. The cell according to claim 10, characterized in that the yeast cell is a methylotrophic yeast cell selected from the group consisting of a yeast of the genus of *Pichia, Candida boidinii* and *Hansenula polymorpha*.

25. The method according to claim 8, characterized in that at least 100 nucleotides of the naturally occurring promoter of the at least one gene encoding the biosynthesis supporting polypeptide or protein is deleted.

26. The cell according to claim 18, characterized in that at least 100 nucleotides of the naturally occurring promoter of the at least one gene encoding the biosynthesis supporting polypeptide or protein is deleted.

27. The cell of claim 19, wherein the polypeptide or protein is disulfide isomerase.

28. The cell of claim 26, wherein the polypeptide or protein is disulfide isomerase.

\* \* \* \* \*